(12) United States Patent
Graves et al.

(10) Patent No.: US 8,589,176 B2
(45) Date of Patent: Nov. 19, 2013

(54) METHODS AND SYSTEMS FOR MANAGING COMMUNICATION REQUESTS IN AN INSTITUTIONAL SETTING SUCH AS A HEALTHCARE FACILITY

(75) Inventors: Alan Graves, Kanata (CA); Jeffrey Ritchett, Kanata (CA); Brian Vezza, Allen, TX (US)

(73) Assignee: Avaya, Inc., Basking Ridge, NJ (US)

(*) Notice: Subject to any disclaimer, the term of this patent is extended or adjusted under 35 U.S.C. 154(b) by 1022 days.

(21) Appl. No.: 12/153,747

(22) Filed: May 23, 2008

(65) Prior Publication Data

US 2009/0147940 A1 Jun. 11, 2009

Related U.S. Application Data

(60) Provisional application No. 60/992,345, filed on Dec. 5, 2007.

(51) Int. Cl.
  *G06Q 10/00* (2012.01)
(52) U.S. Cl.
  USPC .................................................. 705/2; 705/3
(58) Field of Classification Search
  USPC .......................................................... 705/2
  See application file for complete search history.

(56) References Cited

U.S. PATENT DOCUMENTS

| | | | |
|---|---|---|---|
| 4,601,064 A | 7/1986 | Shipley | |
| 5,291,399 A | 3/1994 | Chaco | |
| 5,434,775 A | 7/1995 | Sims et al. | |
| 5,465,082 A | 11/1995 | Chaco | |
| 5,534,851 A | 7/1996 | Russek | |
| 5,544,661 A | 8/1996 | Davis et al. | |
| 5,594,786 A | 1/1997 | Chaco et al. | |
| 5,610,596 A | 3/1997 | Petitclerc | |
| 5,689,229 A | 11/1997 | Chaco et al. | |
| 5,822,544 A * | 10/1998 | Chaco et al. | 705/2 |
| 5,877,675 A | 3/1999 | Rebstock et al. | |
| 5,901,172 A | 5/1999 | Fontana et al. | |

(Continued)

FOREIGN PATENT DOCUMENTS

| | | |
|---|---|---|
| CA | 2263428 A1 | 2/1998 |
| CA | 2362635 A1 | 8/2000 |

(Continued)

OTHER PUBLICATIONS

Office Action mailed on May 16, 2008 in connection with U.S. Appl. No. 11/065,396.

(Continued)

*Primary Examiner* — Hiep V Nguyen

(57) ABSTRACT

A method of processing a communication request destined for an intended recipient, comprising: determining an interrupt worthiness of the communication request; determining an interruptability of the intended recipient; determining at least one delivery feature based on the interrupt worthiness of the communication request and the interruptability of the intended recipient; and causing delivery of the communication request over a communication system in accordance with the at least one delivery feature. Also, a method for monitoring workflows in an institutional environment, comprising: obtaining an indication that a workflow being executed by a particular user has been interrupted by a communication request; determining expected workflow resumption activity associated with the interrupted workflow; monitoring actual workflow resumption activity being executed by a user having resumed the interrupted workflow; carrying out a comparison between the expected and actual workflow activity; and conditionally notifying the user having resumed the interrupted workflow, based on the comparison.

49 Claims, 7 Drawing Sheets

(56) References Cited

U.S. PATENT DOCUMENTS

| | | |
|---|---|---|
| 5,910,776 A | 6/1999 | Black |
| 5,911,687 A | 6/1999 | Sato et al. |
| 5,942,986 A | 8/1999 | Shabot et al. |
| 6,009,333 A | 12/1999 | Chaco |
| 6,026,125 A | 2/2000 | Larrick, Jr. et al. |
| 6,054,950 A | 4/2000 | Fontana |
| 6,211,790 B1 | 4/2001 | Radomsky et al. |
| 6,239,741 B1 | 5/2001 | Fontana et al. |
| 6,259,355 B1 | 7/2001 | Chaco et al. |
| 6,262,662 B1 | 7/2001 | Back et al. |
| RE37,531 E | 1/2002 | Chaco et al. |
| 6,344,794 B1 | 2/2002 | Ulrich et al. |
| 6,462,656 B2 | 10/2002 | Ulrich et al. |
| 6,539,393 B1 | 3/2003 | Kabala |
| 6,577,238 B1 | 6/2003 | Whitesmith et al. |
| 6,662,068 B1 | 12/2003 | Ghaffari |
| 6,690,741 B1 | 2/2004 | Larrick, Jr. et al. |
| 6,753,671 B1 | 6/2004 | Harvey |
| 6,773,396 B2 | 8/2004 | Flach et al. |
| 6,812,884 B2 | 11/2004 | Richley et al. |
| 6,823,199 B2 | 11/2004 | Gough |
| 6,825,763 B2 | 11/2004 | Ulrich et al. |
| 6,870,916 B2 | 3/2005 | Henrikson et al. |
| 6,876,303 B2 | 4/2005 | Reeder et al. |
| 6,958,677 B1 | 10/2005 | Carter |
| 6,958,706 B2 | 10/2005 | Chaco et al. |
| 6,972,683 B2 | 12/2005 | Lestienne et al. |
| 7,042,337 B2 | 5/2006 | Borders et al. |
| 7,080,061 B2 | 7/2006 | Kabala |
| 7,154,397 B2 | 12/2006 | Zerhusen et al. |
| 7,242,306 B2 | 7/2007 | Wildman et al. |
| 7,283,037 B2 | 10/2007 | Diorio et al. |
| 7,603,108 B2 * | 10/2009 | Sparks et al. ............ 455/414.1 |
| 2001/0044731 A1 | 11/2001 | Coffman et al. |
| 2002/0044043 A1 | 4/2002 | Chaco et al. |
| 2002/0044059 A1 | 4/2002 | Reeder et al. |
| 2002/0147912 A1 | 10/2002 | Shmueli et al. |
| 2002/0183078 A1 | 12/2002 | Hase |
| 2002/0183979 A1 | 12/2002 | Wildman |
| 2003/0078810 A1 | 4/2003 | Cole et al. |
| 2003/0078811 A1 | 4/2003 | Cole et al. |
| 2003/0132845 A1 | 7/2003 | McDaniel, III |
| 2004/0001446 A1 | 1/2004 | Bhatia et al. |
| 2004/0004460 A1 | 1/2004 | Fitch et al. |
| 2004/0008114 A1 | 1/2004 | Sawyer |
| 2004/0034284 A1 | 2/2004 | Aversano et al. |
| 2004/0078219 A1 | 4/2004 | Kaylor et al. |
| 2004/0100376 A1 | 5/2004 | Lye et al. |
| 2004/0108954 A1 | 6/2004 | Richley et al. |
| 2004/0153344 A1 | 8/2004 | Bui et al. |
| 2004/0178947 A1 | 9/2004 | Richley et al. |
| 2004/0186357 A1 | 9/2004 | Soderberg et al. |
| 2004/0193449 A1 | 9/2004 | Wildman et al. |
| 2004/0252015 A1 | 12/2004 | Galperin et al. |
| 2004/0257224 A1 | 12/2004 | Sajkowsky |
| 2005/0017864 A1 | 1/2005 | Tsoukalis |
| 2005/0027465 A1 | 2/2005 | Pozsgay et al. |
| 2005/0035862 A1 | 2/2005 | Wildman et al. |
| 2005/0086079 A1 * | 4/2005 | Graves et al. ............ 705/2 |
| 2005/0148831 A1 | 7/2005 | Shibata et al. |
| 2005/0151641 A1 | 7/2005 | Ulrich et al. |
| 2005/0153681 A1 | 7/2005 | Hanson |
| 2005/0168341 A1 | 8/2005 | Reeder et al. |
| 2005/0188095 A1 | 8/2005 | Gardiner et al. |
| 2005/0201345 A1 | 9/2005 | Williamson |
| 2005/0283382 A1 | 12/2005 | Donoghue et al. |
| 2006/0006999 A1 | 1/2006 | Walczyk et al. |
| 2006/0143043 A1 | 6/2006 | McCallie, Jr. et al. |
| 2006/0282459 A1 | 12/2006 | Kabala |

FOREIGN PATENT DOCUMENTS

| | | |
|---|---|---|
| CA | 2373241 A1 | 11/2000 |
| CA | 2434714 A1 | 8/2002 |
| EP | 0 369 662 A2 | 5/1990 |
| EP | 1 101 437 A1 | 5/2001 |
| EP | 1 156 336 A1 | 11/2001 |
| EP | 0 973 316 A3 | 6/2002 |
| EP | 1 536 306 A1 | 6/2005 |
| GB | 2320397 A | 6/1998 |
| GB | 2355889 A | 5/2001 |
| GB | 0602885.6 | 6/2006 |
| GB | 0602887.7 | 6/2006 |
| GB | 0602901.1 | 6/2006 |
| GB | 0602903.7 | 6/2006 |
| GB | 0602904.5 | 6/2006 |
| GB | 0602906.0 | 6/2006 |
| GB | 0602907.8 | 6/2006 |
| JP | 2002157040 A | 5/2002 |
| JP | 2003189359 A | 7/2003 |
| WO | WO 95/01617 | 1/1995 |
| WO | WO 99/04685 | 2/1999 |
| WO | WO 99/64974 A1 | 12/1999 |
| WO | WO 00/52498 | 9/2000 |
| WO | WO 2004/032019 A3 | 4/2004 |
| WO | WO 2004/042563 A3 | 5/2004 |
| WO | WO 2004/102457 A2 | 11/2004 |
| WO | WO 2005/043402 A1 | 5/2005 |
| WO | PCT/CA2006/000203 | 1/2006 |
| WO | PCT/CA2006/000204 | 2/2006 |
| WO | PCT/CA2006/000195 | 5/2006 |
| WO | PCT/CA2006/000196 | 5/2006 |
| WO | PCT/CA2006/000197 | 5/2006 |
| WO | PCT/CA2006/000205 | 5/2006 |
| WO | WO 2006/049728 A1 | 5/2006 |
| WO | PCT/CA2006/000198 | 6/2006 |
| WO | PCT/CA2006/001479 | 12/2006 |

OTHER PUBLICATIONS

Jonathan Collins, "RFID Remedy for Medical Errors", RFID Journal, http://www.rfidjournal.com/article/view/961, May 28, 2004, 3 pages.

Claire Swedberg, "Ford Deploys RFID-Enabled Chargers", RFID Journal, http://www.rfidjournal.com/article/articleview/1348/1/1/, Jan. 19, 2005, 3 pages.

Parco Merged Media Corporation, "The Parco Real Time Location System", http://www.parcomergedmedia.com/whcs_pgis.html, downloaded Feb. 2005, 5 pages.

Parco Merged Media Corporation, "Improving the Availability of Information", www.parcowireless.com, downloaded Jan. 2005, 8 pages.

Parco Merged Media Corporation, "The Parco Wireless Health Care System (WHCS)", www.parcowireless.com, downloaded Aug. 2004, 8 pages.

Robert J. Fontana, Ph.D., "Experimental results from an ultra wideband precision geolocation system", www.multispectral.com, downloaded Aug. 2004, 9 pages.

Robert J. Fontana et al., "Ultra-wideband precision asset location system", www.multispectral.com, downloaded Aug. 2004, 5 pages.

Robert J. Fontana et al., "Commercialization of an ultra wideband precision asset location system", www.multispectral.com, downloaded Aug. 2004, 5 pages.

Dr. Zeev Weissman, "Indoor Location", Tadlys Ltd., www.tadlys.com, downloaded Jul. 2004, 15 pages.

Chronaki et al, "WebOnCOLL: Medical Collaboration in Regional Healthcare Netwoks", IEEE Transactions on Information Technology in Biomedicine,vol. 1, No. 4, Dec. 1997, pp. 257-269.

Rodriquez et al., "Location-Aware Access to Hospital Information and Services", IEEE Transactions on Information Technology in Biomedicine, vol. 8, No. 4, Dec. 2004, pp. 448-455.

Vision > 2015, Canada Health Infoway Inc., "advancing Canada's next generation of healthcare", www.infoway-inforoute.ca, as early as Aug. 14, 2008, 36 pages.

Baker, G. Ross et al., "The Canadian Adverse Events Study: the incidence of adverse events among hospital patients in Canada", © 2004 Cdn. Medical Ass., May 25, 2004, pp. 1678-1686.

Davis, Peter, "Health care as a risk factor", © 2004 Canadian Medical Association, CMAJ, May 25, 2004, pp. 1688-1689.

(56) References Cited

OTHER PUBLICATIONS

Brixey Juliana J. et al., "Towards a hybrid method to categorize interruptions and activities in healthcare", Int'l. Journal of Medical Informatics 76, Sep. 27, 2006, pp. 812-820.

Parker, Julie et al., "Improving Clinical Communication: A View from Psychology", © Hewlett-Packard Company 2000, Jun. 12, 2000, 16 pages.

Alvarez, George et al., "Interruptive communication patterns in the intensive care unit ward round", International Journal of Medical Informatics, Mar. 22, 2005, 6 pages.

Blum, NJ et al., "Interrupted care. The effects of paging on pediatric resident activities.", Am J Dis Child, Jul. 1992, http://www.ncbi.nlm.nih.gov/pubmed/1496947, 1 page.

The OODA "Loop" Sketch, downloaded from http://www.d-n-i.net/boyd_ooda_loop.ppt, © Kettle Creek Corporation, Mar. 13, 2008, downloaded on Sep. 18, 2008.

Laxmisan et al, The multitasking clinician: Decision-making and cognitive demand during and after team handoffs in emergency care, Int'l J of Med Info 76, Sep. 27, 2006, pp. 801-811.

EHRS Blueprint—an interoperable EHR framework—Infoway Architecture Update—Canada Health infoway, Mar. 2006, Solution Architecture Group, 136 pages.

Graves, Alan et al., Applications and Solutions for Healthcare-Hospitals, A Perspective on ECAS, Version 1.0, Dec. 20, 2006, © Nortel Networks 2006, 226 pages.

Bardram, Jacob E., Applications of Context-Aware Computing in Hospital Work—Examples and Design Principles, © 2004 ACM, SAC '04, Mar. 14-17, 2004, Nicosia, Cyprus, 6 pages.

* cited by examiner

METHODS AND SYSTEMS FOR MANAGING COMMUNICATION REQUESTS IN AN INSTITUTIONAL SETTING SUCH AS A HEALTHCARE FACILITY

CROSS-REFERENCE TO RELATED APPLICATION

The present application claims the benefit under 35 U.S.C. 119(e) of U.S. Provisional Patent Application Ser. No. 60/992,345, filed on Dec. 5, 2007, hereby incorporated by reference herein.

FIELD OF THE INVENTION

The present invention relates generally to methods and systems for managing communication requests in an institutional setting such as a healthcare facility.

BACKGROUND

It is known that medical errors can directly or indirectly cause mortality and morbidity. It is also known that many medical errors are committed due, at least in part, to interruptions arising from communication requests (refer to, e.g., *The Multitasking Clinician Decision-Making And Cognitive Demand During And After Team Handoffs In Emergency Care*, Archana Laxmisan, Forogh Hakimzada, Osman R. Sayan, Robert A. Green, Jiajie Zhang, Vimla L. Patel, International Journal of Medical Informatics 76 (2007) pages 801-811; *Improving Clinical Communication: A View From Psychology*, Parker, J. and E. Coiera, J Am Med Inform Assoc, 2000. 7(5): p. 453-461; *Interruptive Communication Patterns In The Intensive Care Unit Ward Round*, Alvarez, G. and E. Coiera, International Journal of Medical Informatics, 74 (2005) pages 791-796; *and Interrupted Care. The Effects Of Paging On Pediatric Resident Activities*, Blum, N. J. and T. A. Lieu, AM J Dis Child, 1992. 146(7): p. 806-8). For example, an interruption arising from a communication request may prevent a clinician from completing an ongoing procedure or treatment, may disturb his or her train of thought during diagnosis, or may force him or her to rapidly hand off the activity to another clinician. These are all error-prone events. There are numerous other examples of scenarios where interruptions arising from a communication request can lead to a medical error being committed, which can negatively impact patient care.

Statistically, many interruptions tend to arise from communication requests that are of relatively low importance or urgency and could therefore be ignored or deferred. However, some interruptions arise from communication requests that pertain to mission-critical events in a healthcare facility (e.g., code blue team formation) and must therefore be responded to immediately and by appropriate personnel. Thus, there is a need in the industry for a method and system for managing communication requests in an institutional setting, with particular application to a healthcare facility where communication requests can come in a wide variety of formats and with varying degrees of criticality and urgency.

Furthermore, there is a need to monitor the workflow on either side of an interruption arising from a communication request in order to detect and prevent potential errors.

SUMMARY

A first aspect of the present invention seeks to provide a method of processing a communication request destined for an intended recipient, comprising: determining an interrupt worthiness of the communication request; determining an interruptability of the intended recipient; determining at least one delivery feature based on the interrupt worthiness of the communication request and the interruptability of the intended recipient; and causing delivery of the communication request over a communication system in accordance with the at least one delivery feature.

A second aspect of the present invention seeks to provide a computer-readable storage medium comprising computer-readable instructions for instructing a computing device to: determine an interrupt worthiness of a communication request destined for an intended recipient; determine an interruptability of the intended recipient; determine at least one delivery feature based on the interrupt worthiness of the communication request and the interruptability of the intended recipient; and cause delivery of the communication request over a communication system in accordance with the at least one delivery feature.

A third aspect of the present invention seeks to provide a system, comprising: a communication request receiving entity configured to receive a communication request destined for an intended recipient; an interrupt worthiness evaluator configured to determine an interrupt worthiness of the communication request; an interruptability evaluator configured to determine an interruptability of the intended recipient; a decision making engine configured to determine at least one delivery feature based on the interrupt worthiness of the communication request and the interruptability of the intended recipient; and a communication request delivering entity configured to deliver the communication request in accordance with the at least one delivery feature.

A fourth aspect of the present invention seeks to provide a system, comprising: means for determining an interrupt worthiness of the communication request; means for determining an interruptability of the intended recipient; means for determining at least one delivery feature based on the interrupt worthiness of the communication request and the interruptability of the intended recipient; and means for causing delivery of the communication request over a communication system in accordance with the at least one delivery feature.

A fifth aspect of the present invention seeks to provide a method for monitoring workflows in an institutional environment, comprising: obtaining an indication that a workflow being executed by a particular user has been interrupted by a communication request; determining expected workflow resumption activity associated with the interrupted workflow; monitoring actual workflow resumption activity being executed by a user having resumed the interrupted workflow; carrying out a comparison between the expected and actual workflow activity; and conditionally notifying the user having resumed the interrupted workflow, based on the comparison.

A sixth aspect of the present invention seeks to provide a computer-readable storage medium comprising computer-readable instructions for instructing a computing device to: be attentive to an indication that a workflow being executed by a particular user has been interrupted by a communication request; determine expected workflow resumption activity associated with the interrupted workflow; monitor actual workflow resumption activity being executed by a user having resumed the interrupted workflow; carry out a comparison between the expected and actual workflow resumption activity; and cause conditional notification of the user having resumed the interrupted workflow, based on the comparison.

A seventh aspect of the present invention seeks to provide a system, comprising: a decision making engine configured to obtain an indication that a workflow being executed by a particular user has been interrupted by a communication request; an institutional context processing engine configured to determine expected workflow resumption activity associated with the interrupted workflow; a situational context processing engine configured to monitor actual workflow resumption activity being executed by a user having resumed the interrupted workflow; the decision making engine being further configured to carry out a comparison between the expected and actual workflow resumption activity and to conditionally notify the user having resumed the interrupted workflow, based on said comparison.

BRIEF DESCRIPTION OF THE DRAWINGS

It is to be expressly understood that the description and drawings are only for the purpose of illustration of certain embodiments of the invention and are an aid for understanding. They are not intended to be a definition of the limits of the invention.

In the accompanying drawings.

DETAILED DESCRIPTION

Figure 1:
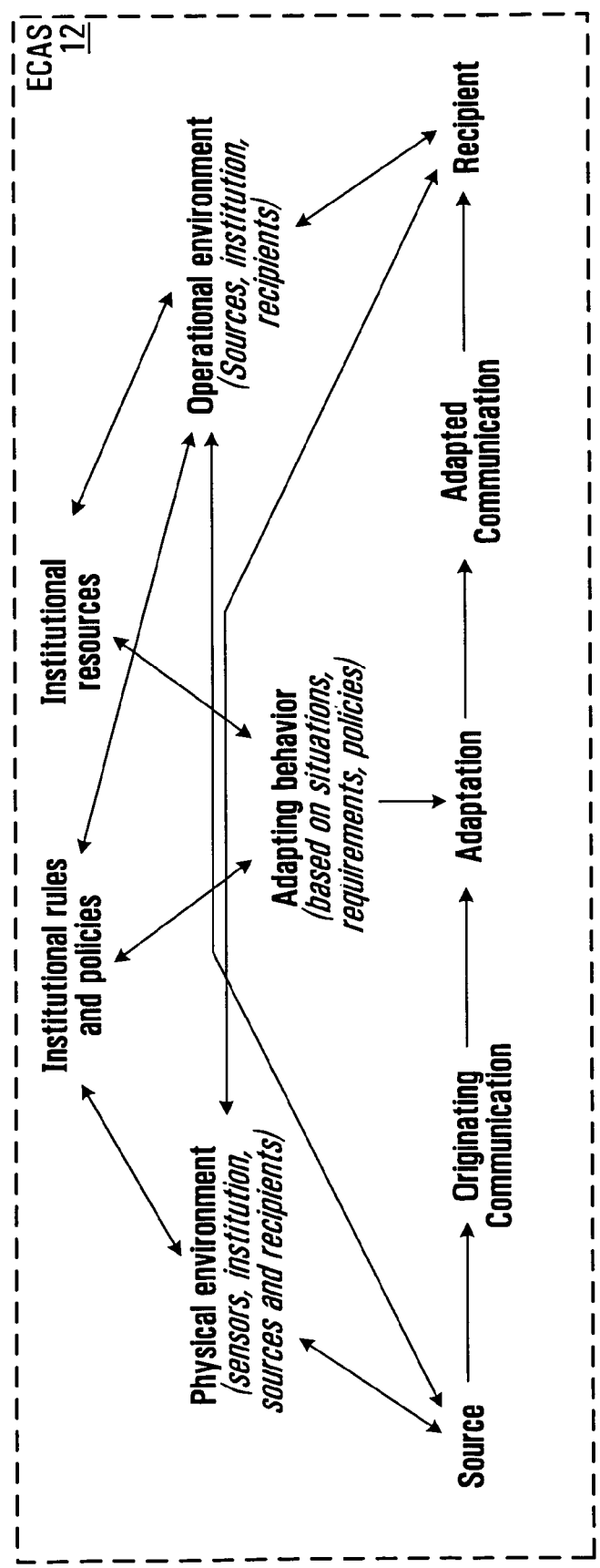
FIG. 1 conceptually illustrates an environment- and context-aware system for providing services in an institutional setting.

In accordance with non-limiting embodiments of the present invention, and with reference to FIG. 1, there is provided an Environment- and Context-Aware communication System (ECAS) 12 with application to a healthcare facility. An understanding of certain basic elements and example functionality of the ECAS 12 can be obtained by consulting the contents of U.S. patent application Ser. No. 12/003,206 to Graves et al. entitled "METHODS AND SYSTEMS FOR USE IN THE PROVISION OF SERVICES IN AN INSTITUTIONAL SETTING SUCH AS A HEALTHCARE FACILITY", filed on Dec. 20, 2007, hereby incorporated by reference herein.

The ECAS 12 utilizes an arrangement of sensors, a communication system as well as access to operational resources, functional resources and institution information from configuration servers, policy servers, user lists and profiles, in order to render significant and useful decisions concerning the provision of services within the healthcare facility. Specifically, the ECAS 12 enables decisions to be made regarding what actions should be taken that are consistent with a particular service, in a given "situational context", based on inputs (e.g. human inputs, feedback, sensors, updated data in database, the changing status of a person/entity, communications status, etc.) relevant to the particular service.

In accordance with one non-limiting example, the "situational context" can be viewed as the collective state of one or more "situations" that each describe a set of circumstances surrounding an event or group of events, the previous history of that event/those events and any associated factors. For example, one "situation" may be "Dr. Jones is administering CPR to Mrs. Smith on the $3^{rd}$ floor", while another "situation" may be "The gas sensor on the $3^{rd}$ floor detected a level of above 1 ppm carbon monoxide for the last 5 minutes". The "situational context" is formed by the collective state of these two (and possibly many other) situations.

As mentioned above, some of the inputs include sensors, which produce sensed data. The sensed data may be the result of location/proximity sensing technology and/or or forms of physical world sensors (e.g. optical, thermal, video, pressure, gas, toxin and biotoxin, vibration/movement, acoustic, various clinical/other specialized and other types of environment-plane sensors). The ECAS 12 can also take into account the status or condition of the communication system itself. In accordance with one non-limiting example, the totality of the "environment" (including locational aspects, thermal aspects, humidity aspects, radiation aspects, etc.) is separated into "planes", the contours of which can be measured by sensors active in that plane. Examples include physical planes such as location/proximity, thermal/temperature, radiation, etc. or may be non-physical, such as authentication status, skills, etc.

The contours between planes can be combined to deduce "plane-rich" perspectives, which provide a heightened environmental awareness, permitting the assessment or identification of situations such as: "Dr. Jones is with Mrs. Smith in a preparation room before surgery and Mrs. Smith is scheduled for surgery within an hour." In this case, knowing further that Dr. Jones is the scheduled surgeon for Mrs. Smith could lead the ECAS 12 to conclude that Dr. Jones is preparing Mrs. Smith for surgery, which can be associated with certain follow-up actions. The integration of multiple planes to create a global (multi-plane) view can be therefore used to monitor, inform, support or instruct users.

The decisions taken by the ECAS 12 can result in adaptation or optimization of communications, which may or may not be to such an extent as to enable improved, enhanced or even new clinical "workflows" and processes to result. This may mean preferentially feeding appropriate information to an authenticated user, preventing communications to an inappropriate user, adapting communications to the circumstances of a user or user equipment, establishing machine-to-machine communication with unattended equipment, initiating communications when certain circumstances arise, modifying the format, timing and/or recipient of a communication request, and so on.

As such, the ECAS 12 can provide adaptive, smart communications, based upon environmental awareness on plural environment-planes (including personnel and equipment location, identity, proximities, physical environments, etc.) and deduced situations. This is combined with an ability to access permissions and authorization/authentication profiles for actual or prospective users (human or machine) as well as other databases including policy and information databases. Thus, services can be provided that adapt to the actual communications needs of legitimate users in the context of both the environment in which they operate and their situations.

Figure 2:
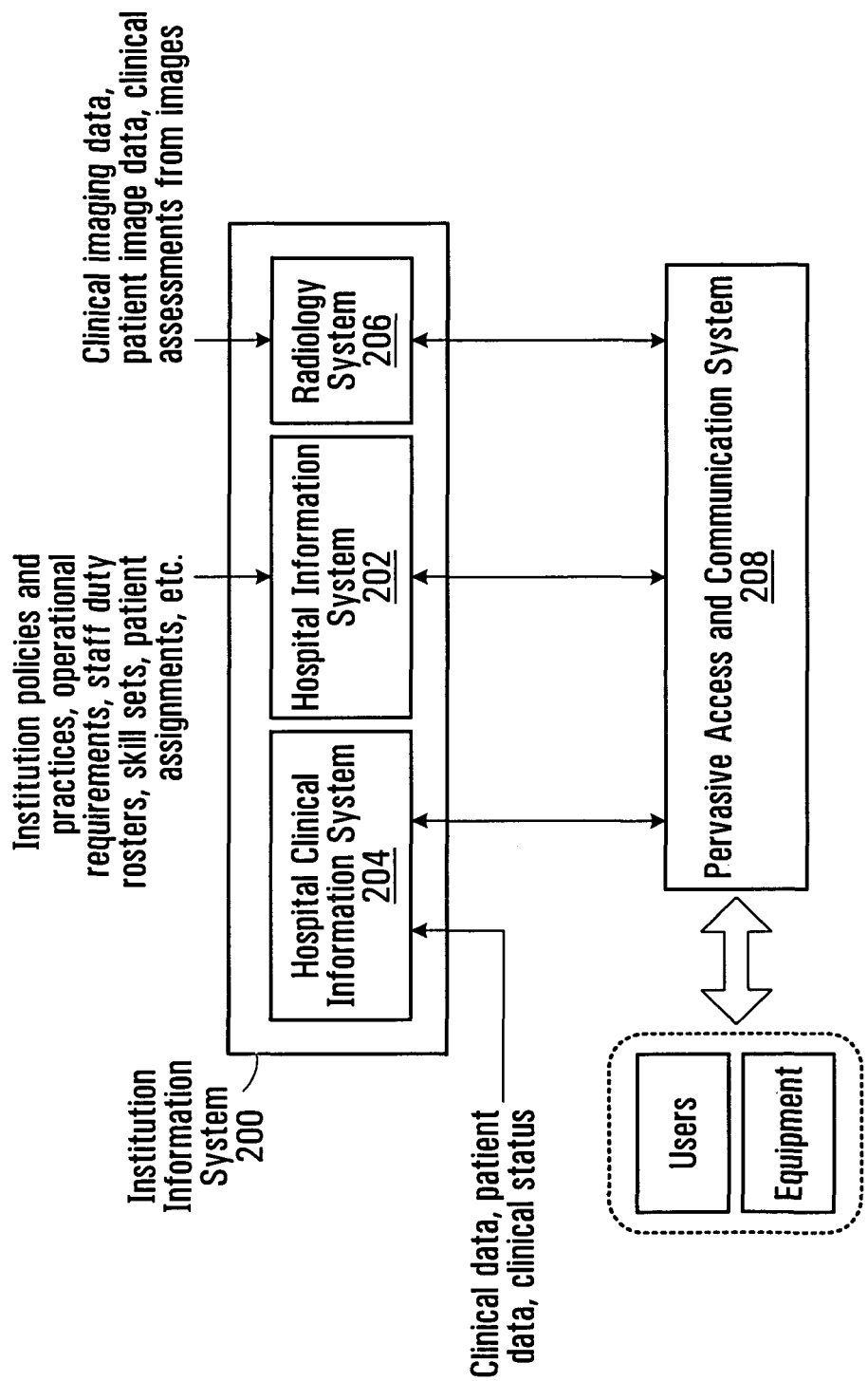
FIG. 2 shows various component features of the information and communication system of a healthcare facility.

Reference is now made to FIG. 2, which shows a healthcare facility such as a hospital, campus or other site. The healthcare facility has a number of component systems, including an institution information system 200 and a pervasive access and communication system 208. In a non-limiting embodiment, the institution information system 200 can be regarded as comprising a hospital information system (HIS) 202, a hospital clinical information system (HCIS) 204 and a radiology system 206. This is a realistic, relevant but simplified view of the actual structures. Each of these systems is now described in some detail.

The HIS 202 may comprise databases for storing a variety of data, examples of which include general institution data, such as financial data, building maintenance schedules, generalized personnel records. Additional examples include work schedules, skill sets (and so on) for clinical and non-clinical staff. Still additional examples include clinical and non-clinical equipment deployment and status. The HIS 202 may also comprise databases for storing information about which clinicians are accredited, what their rights and privileges are, their preferences including their IT preferences, etc. The databases in the HIS 202 may also contain information about healthcare facility support staff, such as orderlies, maintenance staff, administrative staff and biomedical engineers. The databases in the HIS 202 may also contain information about visiting clinicians who have approval to work in the healthcare facility, yet are not formally part of the facility's staff. In this sense, the databases in the HIS 202 can contain information on dynamic/interim users, data, rights and privileges, as well as more formal and more permanent users, data, rights and privileges. Still other examples exist and are included within the scope of the present invention. It is noted that while the databases in the HIS 202 do not contain clinical information about the patient base, they may contain non-clinical data about the patient base.

The HCIS 204 provides storage, processing and retrieval functions for patient/clinical data, much of which is subject to stringent privacy requirements. The HCIS 204 may include the following sub-components:

a HCIS core, which links and supports the clinical databases of multiple departments and databases;

departmental systems, many of which will have been acquired as stand-alone functions and which will have had to have been subsequently integrated together;

local Electronic Patient Records (EPRs) for patients in the healthcare facility or who have been treated by the healthcare facility and which may be linked to the Electronic Medical Records (EMR) of their family physician and/or the patient's own Electronic Health Record (EHR), sometimes referred to as a Personal Health Record (PHR). EMR and EHR are generally considered synonymous, although EMR has a connotation of a discrete, local record while EHR is more global;

test laboratory IT systems and databases with their different functions, modalities and outputs;

firewalled secure gateways out to other locations for connectivity to centralized business continuity/disaster recovery (BC/DR), remote centralized EPR;

entities for implementing sophisticated and stringent access authentication and authorization controls, policies and protocols;

etc.

The above sub-components may comprise databases for storing a variety of data, examples of which include:

policies (which define the responses to be taken under various sets of circumstances and for various services in order to achieve desired results);

lists of entities (such as doctors, nurses, medical equipment) and associated identities (ID) and authentication, authorization and accounting (AAA) information;

patient medical status;

patient test data;

patient schedule data;

patient-clinician association data;

EHR data;

EPR data;

EMR data;

ordered patient treatment data;

diagnosis data;

prognosis data;

staff skills lists;

duty rosters (including off duty personnel who may still be utilized in an emergency of sufficient importance as well as visiting personnel);

workflows;

processes; and regulations/rules.

The above is a non-exhaustive list, as other possibilities remain, and are within the scope of the present invention. The databases in either the HCIS 204 or in the HIS 202 could also store policies which describe minimal and optimal combinations of resources (including people, machines, data, network, etc.) to perform certain functions. For example, the formation of a "Code Blue" team requires certain clinicians and equipment to be reserved within a severely limited time to try and save a patient's life. Other "code names" have their own requirements as well as other processes, for instance to respond to fire, hazardous material releases, lost patients or snatched infants, or to prepare for handling mass casualties in the event of an external disaster. It should be appreciated that although the code names may vary between clinical jurisdictions, a healthcare facility's underlying need for the associated services does not.

The radiology system 206 comprises a suite of non-visible light imaging modalities, such as X-ray, Magnetic Resonance Imaging (MRI), Computed Tomography (CT) scan, Positron Emission Tomography (PET)-scan as well as a Radiology Information System (RIS) which may include a Picture Archiving and Communication System (PACS) to move imaging data between modalities and diagnostic terminals and radiologists as well as archiving and accessing information stored in a radiology information database. The radiology system 206 also system includes diagnostic software aids. Like the HCIS 204, the RIS 206 contains patient clinical data subject to stringent privacy requirements.

The pervasive access and communication system 208 provides access and communication capabilities throughout the healthcare facility, as well as between the healthcare facility and the outside world (not shown) or between geographically dispersed parts of the healthcare facility, such as a hospital split between two campuses. This can be achieved by one or more of the following individual sub-networks:

voice network;

data network;

converged multimedia network: may use Voice over Internet Protocol (VoIP) soft switches to provide voice services, which in turn provides more opportunity for communication sessions via Session Initiation Protocol (SIP);

regional and metro networks: many healthcare facilities have regional operating entities or fall under common administration. Thus, there can be an inter-institutional metropolitan network, which may consist of high-capacity fiber links between healthcare facilities and data centers, for the purposes of data storage, Picture Archiving and Communication System (PACS) and health records systems, disaster recovery, voice communications, etc. The metropolitan network also allows the healthcare facilities to communicate with the Emergency Medical Services (EMS) and city services;

video conferencing and telemedicine network: a specialized infrastructure may exist to support video conferencing and telemedicine systems requiring higher resolution and/or time-sensitive performance;

wireless network: an example of a wireless local area network (WLAN) for voice and data point-of care applications. WLAN-capable user equipment integrate with, for example, nurse call systems which send informative text to the WLAN-capable user equipment as the nurse is being called. Other examples include cell phones or smart phones, which can be used for scheduling and contact in the WLAN;

legacy paging system;

equipment monitoring network: some equipment uses legacy 802.11 standards for point-to-point communications (e.g. wireless electrocardiogram (EKG) monitors). Equipment such as infusion pumps may or may not contain an 802.11 WLAN communications capability; and clinical and virtual private network (VPN) access: satellite clinics access the HIS 202 and HCIS 204 via Ti, digital subscriber line (DSL), or VPN. For remote clinicians, such as outpatient nurses, personal VPN access over the cellular data network can be used.

It should therefore be appreciated that when a sender issues a communication request destined for an intended recipient, this communication request could be received in a variety of formats such as email message, text message, page attempt, call attempt, multimedia message or session, etc. Each delivery format has a respective time-to-human-cognition, which is, for example, virtually instantaneous for a phone call (if the recipient answers the call) and delayed for an e-mail (until the recipient checks his or her e-mail messages). In other embodiments, the intended recipient could be a non-human entity such as machine, robot, database, application, or other entity.

The above is a non-exhaustive list, as other possibilities remain, and are within the scope of the present invention.

Figure 3:
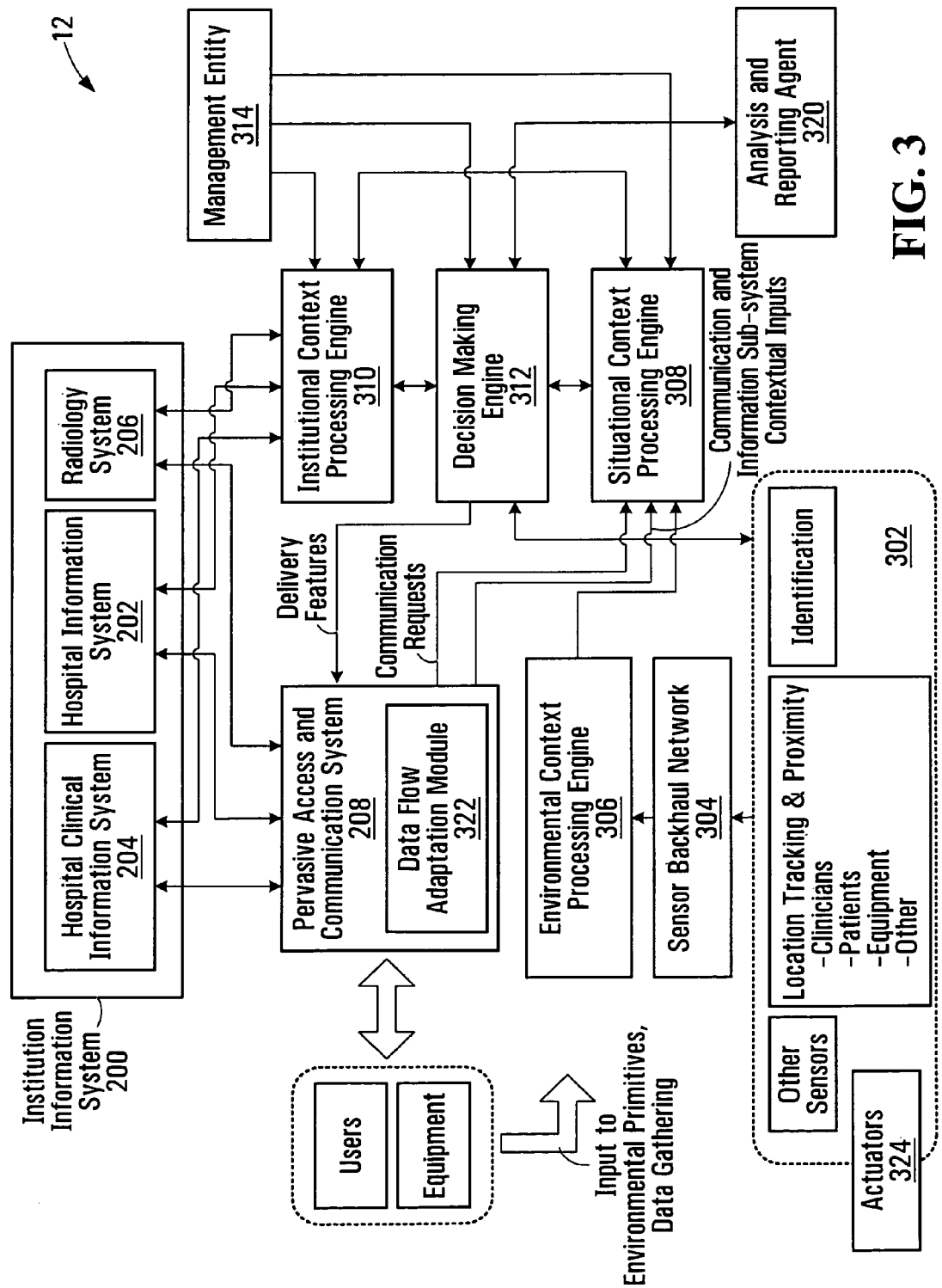
FIG. 3 shows various component features of the information and communication system of a healthcare facility that includes an environment- and context-aware system.

Reference is now made to FIG. 3, which shows the healthcare facility information and communication system of FIG. 2, enhanced with the addition of a number of component systems, including a sensor arrangement 302, a sensor backhaul network 304, an environmental context processing engine 306, a situational context processing engine 308, an institutional context processing engine 310 and a decision making engine 312. Some of these systems can be implemented using hardware, software, firmware, control logic or a combination thereof. It should be appreciated that the context processing engines 306, 308, 310 can be configured and/or reconfigured via one or more management entities 314, such as consoles or terminals for example. This may also occur through self learning systems, analytics, etc. Specifically, the management entities 314 could be accessed by users (such as system administrators) to input algorithms and/or rules that specify the operation of the individual processing engines 306, 308, 310 and/or to monitor system behavior, potentially important to engendering trust in the system.

The sensor arrangement 302 includes sensors for collecting data about each of the environment-planes. These can be designed to include physical sensing capabilities, electro-magnetic transponders and other data-gathering capabilities to interface with various environments. The sensor arrangement 302 may also include actuators coupled to the sensors and having controllable functions.

The sensor backhaul network 304 back-hauls the sensed data from the sensor arrangement 302 to the environmental context processing engine 306. The sensor backhaul network 304 may rely on wired or wireless backhaul. Wired backhaul is generally more dependable but is expensive to install and is often geographically limiting unless the sensor density is low. Both wired and wireless can now offer exceptionally high levels of security. Wireless backhaul is more convenient and can be cheaper but raises issues of the quality and dependability of the RF channel as well as the powering of the sensor node, since powering it over a (presumed non-existent) wired infrastructure may not be an option. Non-limiting examples of wireless access methods include WLAN, ZigBee (IEEE 802.15.4), and Bluetooth. Another method of wireless access, for example for body monitoring sensors, is via Bluetooth or proprietary wireless connections to a wired or wireless terminal. The terminal may contain storage and processing, and has a connection to the environmental context processing engine 306 via the sensor backhaul network 304. This approach may be useful for home and outpatient care.

The sensor data gathered by the sensor arrangement 302 and arriving via the sensor backhaul network 304 is processed by the environmental context processing engine 306 to extract useful information. For instance a single ultrawideband (UWB) receiver output cannot provide the location of a transmitting tag, other than it is somewhere within range of the UWB receiver. However, in the case of a localization function, combining the measurements from multiple (e.g., 3 or more) location receivers allows the location of the tag in 2-D or 3-D space to be pinpointed within a few centimeters of its actual location, typically depending upon the shortness of the duration of the tag's transmitted burst and the timing accuracy in the reception processes in the receivers.

To this end, the environmental context processing engine 306 may be configured to perform the following:

edge functions. These include sensor collection, processing, and encapsulation functions performed at the edge of an IP network. These may also include QoS processing, priority tagging, real-time control, filtering, and content pre-processing; and sensor system virtualization. This includes creating common representations of the sensed data. This also includes processing and amalgamation of lower-level data.

The above is a non-exhaustive list, as other possibilities remain and are within the scope of the present invention.

By way of a specific non-limiting example, the environmental context processing engine 306 may implement simple functions such as detecting activity of a basic environmental parameter relevant to a simple service provided in or by the healthcare facility, such as monitoring location or temperature. By way of another specific non-limiting example in relation to a more complex service provided in or by the healthcare facility, the environmental context processing engine 306 may provide a sophisticated, precise ability to calibrate and relate the activity in or across multiple environments or factors such as location/proximity, temperature, pressure, radiation levels and types, the presence of various hazards (smoke, toxic gases or chemicals, harmful radiation, bio-toxins, etc.). In either case, the environmental context processing engine 306 transforms the sensed data into data indicative of an environmental context in which the activity is deemed to occur.

Often it is useful to compare, correlate, or review the extracted information from one sensor with that from other sensors, either or both operating in the same environment-plane or in other environment-planes, in order to make a situational determination. This is the responsibility of the situational context processing engine 308. Specifically, the output of the environmental context processing engine 306 (i.e., the data indicative of the environmental context) is fed to the situational context processing engine 308 along with other inputs, including from the pervasive access and communication system 208 and selected data from the HIS 202, HCIS 204 and radiology system 206. As mentioned above, the data indicative of the environmental context reflects an activity that is considered relevant to a particular service being provided in/by the healthcare facility.

The situational context processing engine 308 is configured to transform the data indicative of the environmental context into data indicative of a situational context in which a sensed activity is deemed to have occurred. The situational context can be derived not only from the output of the environmental context processing engine 306, but also from activity of the pervasive access and communication system 208 (e.g., communications requests and data passing therethrough) and potentially other information. A non-limiting example of such other information includes an institutional mapping of location to use/scope of activity. For instance, "coordinates (142, 159, 34) are 50 cm north of the operating table in Operating Room 3A (precisely where the anesthetist is supposed to be) and Operating Room 3A is currently scheduled for active surgery".

In a specific non-limiting example, activity of the pervasive access and communication system 208 may signal communications presence, which is an indication of a willingness and ability to communicate. Basic communications presence tells the situational context processing engine 308 if a given clinician is online or offline and if he/she is active within the pervasive access and communication system 208. Communications presence can be more sophisticated, such as identifying the current level or type of activity, such as "active in a meeting" or "do not disturb—in operating room." Some of this information may be manually input by a user or it could also be derived based on, for example, the duty roster of the surgeon combined with his/her location and perhaps those of other clinicians if it is a complex surgery. It can also include some of the items below, either processed or in raw form:

Device Type and Device Capabilities
  This information answers questions such as "Is it a PDA, mobile WLAN phone or laptop", "Does it have, a camera and/or a display capability appropriate for the message?", "What state is the device in?", "What is the current modus operandi?", "What functions can be controlled by the system, e.g., can it be muted?" Clinical mobile devices may require a "privacy" mode.

Bandwidth Availability and Usage
  This is useful for priority or quality of service requirements and may define the nature of the information transfer.

Service Type and Session Type
  This information answers questions such as "Is a voice, video, or data session in progress?", "Can it be interrupted for an urgent call, such as a nurse call or emergency Code call?" (or "What level of urgency and importance in the interrupting message would be required to trigger an immediate or deferred interruption?") and "What are the required connectivity, network quality and terminal capabilities to successfully deliver this service?"

Entity Status
  The nature of this information can be considered from two perspectives. First, where an entity within a system is a machine, "entity state" is the state of the machine. For example the state of a medical instrument: Is the machine operational? Are there any alarms? What is its maintenance status? Second, where a software agent is interacting with a communications system, there are many analogies between "entity state" and "communication presence"; hence the term "entity presence" can be used.

Thus, by combining certain outputs of the environmental context processing engine 306 and the pervasive access and communication system 208, the situational context processing engine 308 determines a situational context. As described earlier, the "situational context" can be viewed as the collective state of one or more situations that each describe a set of circumstances surrounding an event or group of events, the previous history of that event/those events and any associated factors.

As such, the situational context can reflect simple traffic loads and availability of resources or more detailed information such as which users are accessing which classes of information or which users are accessing which servers or even which groups of users are, from a network attachment perspective, in the same general vicinity.

The situational context can also be extended to deducing or estimating the status of a workflow involving a particular clinician/patient encounter by examination of the nature, frequency and destination of information flows to and from the clinician, as well as partial (e.g., patient identity, clinician identity) or comprehensive (e.g., patient condition, clinical situation, clinical workflow situation derived from message contents) examination of the clinical information being transmitted (with the appropriate security and privacy safeguards in place). In a non-limiting example, a "workflow" can be viewed as a sequence of tasks in a procedure or process involving one or more parties, including the task currently being performed and tasks to be performed in the future by any of the parties.

The situational context processing engine 308 produces an output (i.e., data indicative of the situational context) that allows downstream decisions to be made whose relevance/validity increases with the precision and accuracy of environmental characterization data as well as the comprehensiveness of environmental sight. For instance an environmental visibility of only location information is not as useful as having visibility of location, heat profile, toxic gas and smoke distribution and visible or infra-red radiation in a scenario where a fire has occurred and the ECAS 12 is responding to that emergency scenario.

There is also a need for appropriate levels of precision and accuracy for each situation. This can be important since for some workflows are highly sensitive to the relative location of a person with respect to another person or object, as well as their absolute location. Precision and accuracy are not the same thing. While precision can be viewed as the tolerance on the location, accuracy can be viewed as the percentage of times the measured location is less than a certain error distance from the actual location. Hence, a location system may have a precision of +/−1 meter at an accuracy of 99.999% but a precision of 10 cm at an accuracy of 50-%. To take a practical example, consider that a tablet PC may be associated with a clinician when the tablet PC is detected as being within the personal zone of the clinician—which can extend for 50 to 100 cm or even more around him/her, primarily being in front of the clinician. A location system with a precision of +/−160 cm will not work properly in this scenario because it is too imprecise, whereas one with a precision of +/−10 cm is expected to work adequately.

Since the tablet PC may be used for sensitive data, the situational context engine 308 has to accurately associate the clinician to the tablet PC which means that, if the location system is to be the main determinant of this, it must have a very high accuracy (e.g., 99.99%). For this reason knowledge of the tablet PC's location (or other environmentally derived authentication datum) may form part of an authentication process rather than the whole process. Nevertheless it can radically simplify the rest of the process, thereby reducing user fatigue, and can provide safeguards against the rest of the process making errors. For instance if Dr. Smith is on the $3^{rd}$ floor and suddenly his ID is being used to access the system from the $15^{th}$ floor it is likely that an illegal or illicit activity is under way based upon a stolen, duplicated or misappropriated ID and appropriate safeguards can be taken. However, if Dr. Smith accesses the system from the $3^{rd}$ floor and then is tracked transiting to the elevator, entering the elevator, which then ascends to the $15^{th}$ floor and he is then tracked exiting the elevator the situational context will be such that Dr. Smith has moved floors—the overall continuance of appropriate situational context differentiates these two scenarios since in the first scenario many steps would be missing.

The output of the situational context processing engine 308 (i.e., the data indicative of a situational context) is provided to the decision making engine 312.

The decision making engine 312 is configured to apply an "institutional context" to the data indicative of the situational context in order to determine an action to be taken in accordance with provision of the service. In accordance with a non-limiting example, the institutional context can be viewed as what the institution anticipates, requires or expects to happen (or to have happened), based on policies and procedures, in response to individual or combinational determinations of situational context (namely, by the situational context processing engine 308). In a specific scenario, the institutional context can be based on data that is non real-time and input to databases based on institutional policy.

In order to determine which institutional context is relevant to the decision being made by the decision making engine 312, the institutional context processing engine 310 is used. Specifically, the institutional context processing engine 310 interfaces with the HIS 202, HCIS 204 and radiology department 206 via an underlying communications network (not shown), over which raw data and policy frameworks are provided to the decision making engine 312. There may be a number of smaller institutional context engines that focus on specific domains (e.g. nursing, personnel related systems, policies for groups A and B, but possibly not C, etc.). These smaller institutional context engines could collectively be accessed by the decision making engine 312, there could be a form of institutional context fusion or there could be hierarchical structures in place, as well as combinations of the above, and other, options.

The decision making engine 312 implements coordination and processing functions, associated with a set of policies, which makes context decisions and adapts the behaviour of the pervasive access and communications network 208, for each service being provided. To this end, the decision making engine 312 can implement one or more rules engines. The decision making engine can be implemented by a number of non-limiting methods, for example a simple rules-based engine that is programmed by an operator, a fuzzy-logic base engine that is programmed and overseen by an operator, or a self-learning engine of either type that is overseen by an operator through a situational management system.

One example of a possible outcome of the decision making engine 312 is a decision to carry out a communication action, either directly or by sending instructions to the pervasive access and communication system 208 to carry out that communication action. To this end, a data flow adaptation module 322 (shown in FIG. 3) can be provided in the pervasive access and communication system 208 for receiving instructions from the decision making engine 312 and carrying out the desired communication action.

By way of non-limiting example, a communication action may be as simple as denying access to a user based on the assessment that this is not a legitimately authenticated user or it may be the rearrangement of communications services on behalf of a clinician, based upon where that clinician is, who they are with or what they are doing.

Other non-limiting examples of a communication action may include the following:
  initiating a communication (e.g., forming a Code Blue team, initiating a session between clinicians, allowing a clinician with a specific patient to access a certain level of that patient's data and to make certain changes or entries based upon the stage of the patient's treatment, the role of the clinician as well as the patient's and clinician's ID and location, etc.);
  modifying a new or an ongoing communication;
  terminating an ongoing communication; and
  blocking an attempt to establish a communication (e.g., blocking access to files where permissions are inappropriate, etc.);
  modifying the structure, format, timing and/or intended recipient of a communication request originated by a sender, based on a set of delivery features received from the decision making engine 312;
  modifying the structure, format, delivery method of a communication to match the capabilities of a recipient's communications device(s) or the recipient's preferred communication device as a function of their current clinical situation or location.

Another example of a possible outcome of the decision making engine 312 is a decision to modify sensor capabilities or trigger actuators 324. Where the healthcare facility is a hospital, for example, closed loop control might focus security cameras on an event, or lock doors (e.g. to prevent theft) or unlock doors (e.g. to provide a more direct route for a "Code Blue" responding clinician to reach the incident site).

A further example of a possible outcome of the decision making engine 312 is a decision to change a parameter that is used as an input by another service. This creates an interrelatedness among the services being provided by the ECAS 12, which is discussed later on in this specification.

In addition, the decision making engine 312 may also communicate with or implement an analysis and reporting agent 320 that records the various decisions taken.

The preceding description of the ECAS 12 applies to a clinical setting where information is collected about (i) environmental activity; (ii) communication activity; and (iii) situational context of these activities. This information is combined with institutional context, specifically information around facility resources and—under a security blanket— patient clinical information. As such, the ECAS 12 gains intelligence about specific activities and interactions occurring within the healthcare facility.

Figure 4:
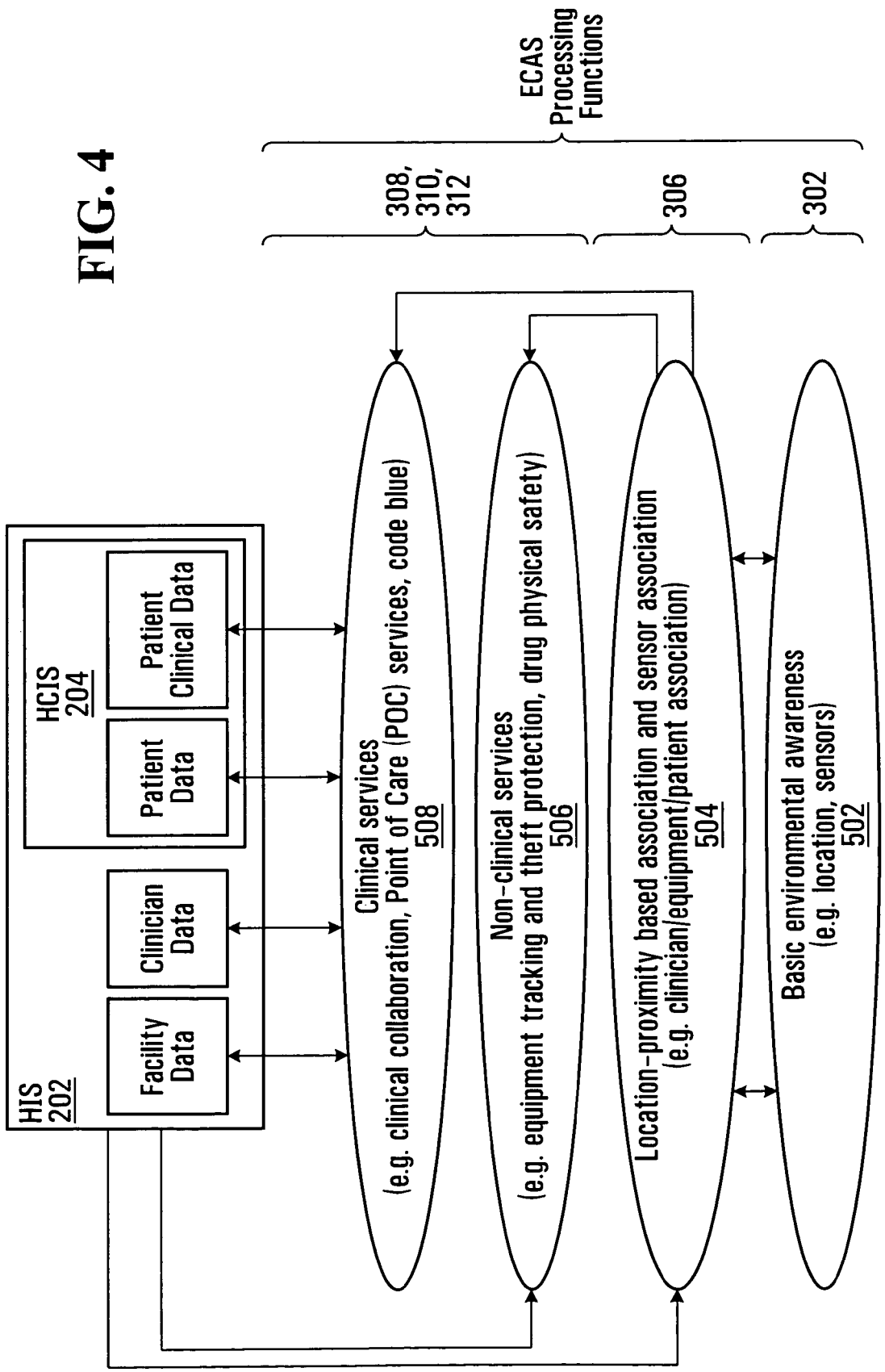
FIG. 4 depicts categorization of the services provided by the environment- and context-aware system.

This intelligence allows the ECAS 12 to provide various services. These services are interrelated and, for example, can be categorized as clinical or non-clinical, as well as routine or emergency. Reference is made to FIG. 4, for example, which provides a complementary view of the ECAS 12 to that of FIG. 3. Specifically, at layer 502, individual services being provided by the ECAS 12 are associated with detection by the sensor arrangement 302 of activity relevant to the provision of each particular service, thereby to generate sensed data. At layer 504, the environmental context processing engine 306 provides location- and proximity-based association and sensor association by transforming the sensed data (which has been sensed as a result of the activity) into data indicative of an environmental context in which the activity is deemed to have occurred. The data indicative of the environmental context is processed in a specific way, depending on whether the service is clinical (layer 508) or non-clinical (layer 506).

One example of a service that can be provided by the ECAS 12 at the non-clinical layer 506 is a communication request management service. This service controls the timing, nature and delivery of the communications based not only upon circumstances and parameters relating to the sender of the communication request but also upon circumstances and parameters relating to the intended recipient. Specific non-limiting examples of these circumstances and parameters will be provided herein below. Consideration of these circumstances and parameters by the decision making engine 312 allows the management of interruptions with minimal impact on the tasks being performed (or scheduled to be performed) by the interruptee at the time of the interruption.

Figure 5:
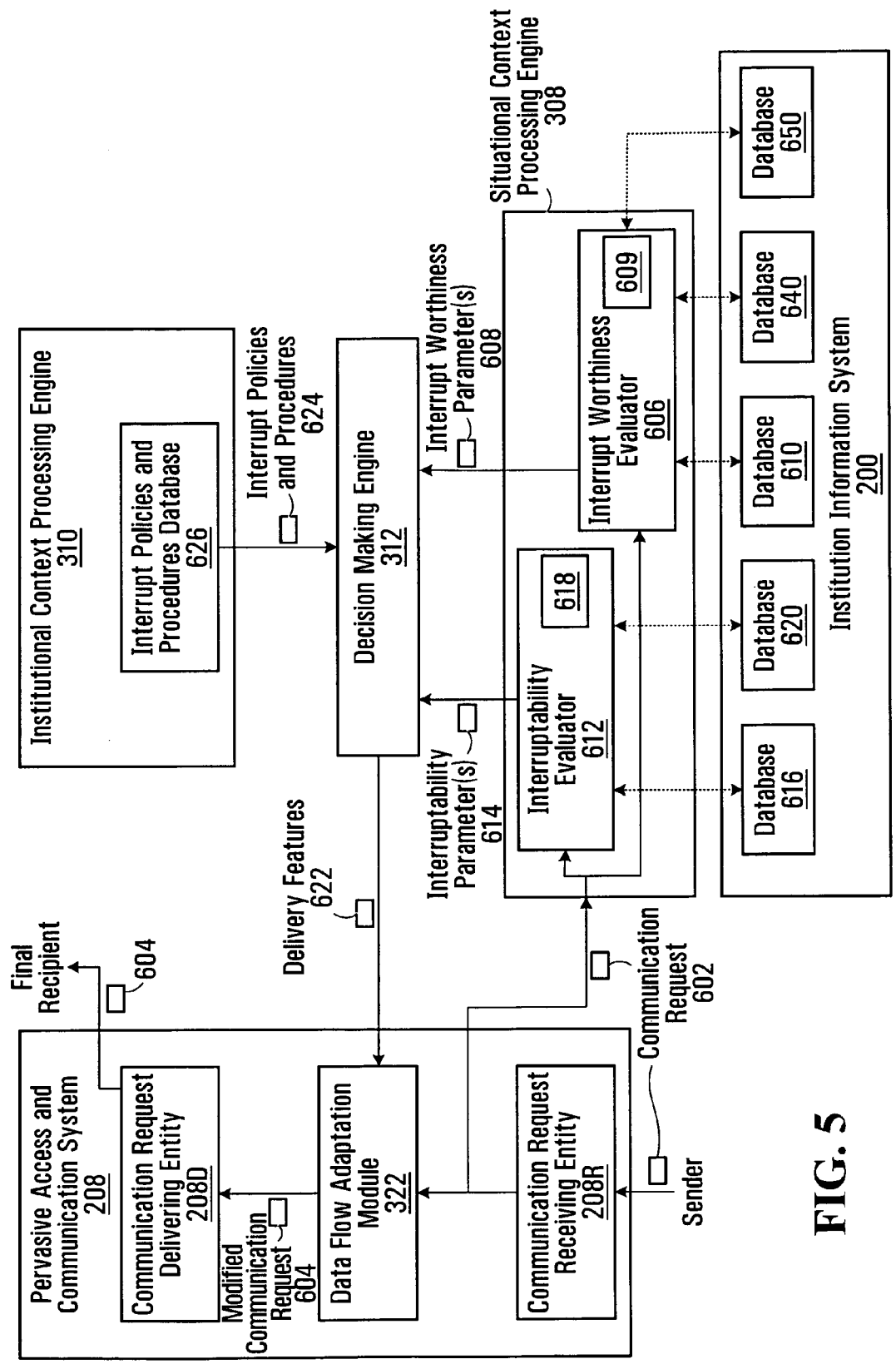
FIG. 5 is a block diagram depicting entities of the environment- and context-aware system that participate in the provision of a communication request management service, in accordance with a non-limiting embodiment of the present invention.

Accordingly, reference is made to FIG. 5, which shows in greater detail certain entities involved in managing a communication request 602 destined for an intended recipient. The communication request 602 is generated by a sender and is received in the pervasive access and communication system 208 by a communication request receiving entity 208R, such as a first arrangement of links, nodes and switches in the pervasive access and communication system 208. The communication request 602 could be received in a format such as email message, text message, page attempt, call attempt, voice mail message, multimedia session or message, etc.

The communication request receiving entity 208R feeds the communication request 602 to the data flow adaptation module 322 as well as the situational context processing engine 308. The data flow adaptation module 322 is configured to transform the communication request 602 into a modified communication request 604 having certain delivery features specified by the decision making engine 312, based upon the analytic inputs from both the situational context processing engine 308 and the institutional context processing engine 310, as will be described herein below. The modified communication request 604 is then delivered to a final recipient over the pervasive access and communication system 208 by a communication request delivering entity 208D, such as a second arrangement of links, nodes and switches in the pervasive access and communication system 208. In one embodiment, the final recipient to whom the modified communication request 604 is delivered is the intended recipient of the communication request 602. In another embodiment, the final recipient to whom the modified communication request 604 is delivered is an alternate recipient. In yet another embodiment, the modified communication request 604 is delivered to several final recipients.

Interrupt Worthiness

As mentioned above, the communication request 602 may be in a format such as email message, text message, page attempt, call attempt, voice mail message, multimedia session or message, etc. Thus, it will be apparent that in all cases, the communication request 602 identifies the intended recipient, while in many instances, the communication request 602 also identifies the sender and in some instances (for example, email messages) it may also include a message from the sender. The identity of the intended recipient, the identity of the sender (if available) as well as the message (if available), are provided to an interrupt worthiness evaluator 606, which determines an interrupt worthiness of the communication request 602 as described in greater detail below. The interrupt worthiness evaluator 606 may be implemented as part of the situational context processing engine 308, or as a stand-alone entity.

In one embodiment, the interrupt worthiness of the communication request 602, as determined by the interrupt worthiness evaluator 606, can be represented by a set of one or more interrupt worthiness parameters 608, which are derived from "intrinsic" information and "extrinsic" information.

Specifically, "intrinsic" information is information that forms part of the communication request 602, such as:
  identity of sender;
  identity of intended recipient;
  message contained in the communication request (if any);
  ancillary information provided by the sender, such as:
    sender-specified importance of communication request;
    sender-specified urgency of communication request;
    sender-specified level of confidentiality/privacy of communication request;
    sender-specified recipient specificity of communication request (e.g., "this request must be answered by Dr. Jones" or "this request can be answered by any cardiologist").

On the other hand, "extrinsic" information is determined by the situational context processing engine 308 based on access to the HIS 202 and the HCIS 204 via the institutional context processing engine 310. Extrinsic information can fall into various categories. For example, extrinsic information could include situational information regarding the intended recipient, such as:
  location of intended recipient;
  location of patients associated with intended recipient;
  skill set of intended recipient;
  schedule of intended recipient;
  actual workflow situation of intended recipient (which may or may not match his/her schedule, i.e., it may be time-offset from the schedule by an arbitrary amount).

Extrinsic information could also include situational information regarding the sender, such as:
  location of sender;
  location of patients associated with sender;
  skill set of sender;
  schedule of sender;
  actual workflow situation of sender (which may or may not match his/her schedule, i.e., it may be time-offset from the schedule by an arbitrary amount);
  specific sender/recipient relationships (e.g., hierarchical);
  emotional or physical state of the sender (e.g., measured by video analysis or body sensors).

Extrinsic information could also include historical information, such as:
  history of communication requests by sender/to intended recipient.

Extrinsic information could also include environmental information, such as:
  safety/severity of weather and other environmental conditions;
  severity of emergency conditions in vicinity of healthcare facility.

Extrinsic information could also include other information, such as:
  executive override.

The interrupt worthiness evaluator 606 synthesizes the intrinsic information and extrinsic information mentioned above, and determines the set of interrupt worthiness parameters 608. Non-limiting examples of the interrupt worthiness parameters 608 can include:
- importance of communication request;
- urgency of communication request;
- specificity of communication request;
- degree of life impact or workflow criticality of communication request.

It should be appreciated that where the communication request 602 contains a message, this can be helpful in allowing the interrupt worthiness evaluator 606 to arrive at a more accurate evaluation of the interrupt worthiness parameters 608. For example, the message may contain an x-ray image of an injury, from which the severity of the injury (and hence the importance and/or urgency of the associated communication request 602) may be derived. In another example, the message may contain a mention of a feature or expression numerous times, which could lead to a conclusion that the communication request 602 is important or urgent.

The above list of interrupt worthiness parameters 608 is not exclusive. Conversely, a reduced number of interrupt worthiness parameters 608 can be determined by the interrupt worthiness evaluator 606. For added understanding, the above-listed interrupt worthiness parameters 608, as well as non-limiting example ways in which they can be derived, are now described in greater detail.

Importance and Urgency

It should be appreciated that "importance" can be discriminated from "urgency". An important communication request requires thoughtful consideration and/or has high impact, while an urgent one requires immediate consideration. A communication request may thus be important without being urgent, or be urgent without being important, or indeed it may be both urgent and important, or neither. Moreover, various types, levels or degrees of importance and urgency are possible. For instance a message may be clinically important (e.g., "shortage of functional and available infusion pumps") or may be important for entirely non-clinical reasons (e.g., "patient insurance is invalid"). In order to obtain an indication of importance and/or urgency of the communication request 602, the interrupt worthiness evaluator 606 may implement a message processing function 609 that is capable of determining contextual information about the communication request 602. For example, if the communication request 602 included a message pertaining to a particular procedure and a particular patient, then the message processing function 609 of the interrupt worthiness evaluator 606 may be configured to determine that the communication request 602 pertains to the particular procedure and the particular patient.

The interrupt worthiness evaluator 606 may then consult a database 610 in the institution information system 200 in order to determine the importance and/or urgency of the communication request 602 based on the contextual information that it was able to derive. Accordingly, for example, the database 610 may associate different procedures to corresponding degrees/levels of urgency (e.g., "in the absence of other urgency-discriminating aspects, then a communication request pertaining to heart surgery is more urgent than one pertaining to a coffee spill in the cafeteria"), or different patients to corresponding degrees/levels of importance (e.g., "in the absence of other importance-discriminating aspects, then a communication request pertaining to a patient with an untreated head wound is more important than one pertaining to a patient with an in-grown toenail"). In addition, for example, the database 610 may include associations between different potential senders and corresponding degrees/levels of importance (e.g., "in the absence of other importance-discriminating aspects, then a communication request from sender X is more important than one from sender Y"), or between different hierarchical positions of potential senders' relative to potential recipients and corresponding degrees/levels of importance (e.g., "in the absence of other importance-discriminating aspects, then a communication request from a sender who is the intended recipient's superior is more important than one from a sender who is the intended recipient's subordinate", although the subordinate's response to a superior's request may carry the importance of the superior, dependent upon the healthcare facility's policy).

It should also be appreciated that the urgency and/or importance of the communication request 602 could be based wholly or partly on the ancillary information provided by the sender (such as "sender-specified importance of communication request" and "sender-specified urgency of communication request").

Specificity

The interrupt worthiness evaluator 606 may also be configured to determine a specificity associated with the communication request 602. For example, the interrupt worthiness evaluator 606 may perform a semantic processing operation to establish whether the communication request 602 is destined only for the intended recipient, or may be sent to (and handled by) other recipients, as determined by the context and contents of the communication request, especially if the communication request includes a message containing patient-identifiable clinical data subject to privacy protection. The specificity can be of assistance to the decision making engine 312 when deciding whether to consider alternate recipients for the modified communication request 604.

It should also be appreciated that the specificity of the communication request 602 could be based wholly or partly on the ancillary information provided by the sender (such as "sender-specified level of confidentiality/privacy of communication request" and "sender-specified specificity of communication request" mentioned earlier).

Degree of Life Impact or Workflow Criticality

The interrupt worthiness evaluator 606 may also be configured to determine a degree of life impact or workflow criticality associated with the communication request 602 by deriving a variety of contextual information. For example, the interrupt worthiness evaluator 606 may consult a database 640 in the institution information system 200 in order to determine information about the workflow being executed by the sender. The interrupt worthiness evaluator 606 may also keep track of the sender and the intended recipient of the communication request 602.

The interrupt worthiness evaluator 606 may then consult a database 650 in the institution information system 200 in order to determine the degree of life impact or workflow criticality of the communication request 602 based on the contextual information that it was able to derive. Accordingly, for example, the database 650 may store information allowing different workflows and intended recipients to be mapped to corresponding degrees of life impact or workflow criticality. Thus, for example, the database 650 may store information that will lead the interrupt worthiness evaluator 606 to conclude that a communication request originating from an emergency room during ongoing brain surgery and intended for a second neurosurgeon has a higher degree of life impact or workflow criticality than a communication request originating from the staff lunch room during lunchtime and intended for an obstetrician.

Interruptability

Also provided in FIG. 5 is an interruptability evaluator 612, which determines an interruptability of one or more potential recipients as described in greater detail below. The interruptability evaluator 612 may be implemented as part of the situational context processing engine 308, or as a stand-alone entity. In one embodiment, the interruptability evaluator 612 operates by continually monitoring the interruptability of all potential recipients. In another embodiment, the interruptability evaluator 612 operates by determining the interruptability of a particular potential recipient (such as the intended recipient) when requested to do so (e.g., by the decision making engine 312, or based on the identity of the intended recipient provided as part of the communication request 602).

In one embodiment, the interruptability of a particular potential recipient, as determined by the interruptability evaluator 612, can be represented by a set of one or more interruptability parameters 614, which are derived from extrinsic information. Extrinsic information is determined by the situational context processing engine 308 based on access to the HIS 202 and the HCIS 204 via the institutional context processing engine 310. Extrinsic information can fall into various categories. For example, extrinsic information could include situational information regarding the intended recipient, such as:
  workflow criticality profile of potential recipient (i.e., "How does the criticality of the workflow vary over near-term future time?");
  workflow temporal profile of potential recipient (i.e., "How does the workflow sequence of events unfold over near-term future time", "When does the current activity end?");
  potential recipient's duration on shift;
  specific sender/recipient relationships (e.g., hierarchical);
  location of potential recipient;
  location of patients associated with potential recipient;
  potential recipient's skill set;
  schedule of potential recipient;
  actual workflow situation of potential recipient (which may or may not match his/her schedule, i.e., it may be time-offset from the schedule by an arbitrary amount. It is noted that being behind schedule can be associated with a higher likelihood of dealing with unanticipated complications and therefore of higher stress);
  emotional or physical state of the potential recipient (e.g., measured by video analysis or body sensors).

Extrinsic information could also include environmental information, such as:
  safety/severity of weather and other environmental conditions;
  severity of emergency conditions in vicinity of healthcare facility;

Extrinsic information could also include other information, such as:
  executive override.

Still other factors will be apparent to those of skill in the art as being within the scope of the present invention.

The interruptability evaluator 612 synthesizes the extrinsic information mentioned above, and determines the set of interruptability parameters 614. Non-limiting examples of the interruptability parameters 614 can include:
  criticality level of current and next/future task(s) (e.g., "How critical in term of urgency and/or importance is the current task within the overall workflow?" or "Will the workflow stall if the person is interrupted?")
  interruptability profile (e.g., mapping of predicted interrupt tolerance over future time);
  list of preferred interrupters;

The above list of interruptability parameters 614 is not exclusive. Conversely, a reduced number of interruptability parameters 614 can be determined by the interruptability evaluator 612. For added understanding, the above-mentioned interruptability parameters 614, as well as various non-limiting example ways in which they can be derived, are now described in greater detail.

Criticality Level of Current and Next/Future Task(s) and Interruptability Profile In order to determine the criticality level of current and next/future task(s) and the interruptability profile pertaining to a particular potential recipient, the interruptability evaluator 612 needs to determine the task being currently performed by the particular potential recipient and the workflow in which the particular potential recipient is involved. To this end, the interruptability evaluator 612 may consult a database 616 in the institution information system 200. The database 616 may associate potential recipients to tasks currently being performed, and the workflows to which those tasks belong. In a specific non-limiting example, the information returned by the database 616 when queried with the identity of the particular potential recipient may include a series of tasks that are associated with a surgical procedure (e.g., "open-heart surgery"), and the task being currently performed by the particular potential recipient (e.g., "scrubbing in"). Alternatively, the database 616 can be omitted, and the requisite information derived directly from the situational context processing engine 308 and/or the institutional context processing engine 310.

The interruptability evaluator 612 may implement a workflow analysis function 618 that is capable of determining one or more of the aforementioned interruptability parameters 614 based on the task being currently performed by the particular potential recipient and the workflow including that task, as obtained from the database 616. To take the above example, if the particular potential recipient is currently performing the task of "scrubbing in" for the workflow of "open-heart surgery", then the workflow analysis function 618 of the interruptability evaluator 612 may be configured to determine that the criticality level of current and next/future task(s) is currently "low" (since scrubbing in is a non-clinical activity) but will momentarily become "high" and that the interruptability profile will then be "very low (i.e. low tolerance for being interrupted) for several hours, followed by moderate for 1 hour". To take a contrasting example, if the particular potential recipient is studying a patient's chart at the end of his rounds, then the workflow analysis function 618 of the interruptability evaluator 612 may be configured to determine that the criticality level of current and next/future task(s) is "medium" and that the interruptability profile is "high (interruptions likely to be well tolerated) for the remainder of shift".

It should be appreciated that individual users may or may not be allowed to set their own, customized interruptability profile according to facility policy and their history of communication.

List of Preferred Interruptors

The interruptability evaluator 612 may also consult yet another database 620 in order to obtain, for each potential recipient, a list of potential senders (referred to herein as "preferred interrupters") having a higher priority of interrupt relative to other senders who are not on the list. More generally, it is within the scope of the present invention for the database 620 to store, for a given potential recipient, a more granular Preference Level (e.g., on a scale of 0—least preferred to 9—most preferred, from the perspective of the given potential recipient) for one, several or all potential senders. The Preference Level for a given combination of a potential sender and a potential recipient can thus represent a tolerance of the potential recipient to being interrupted by the potential sender.

Decision Making Process

The interrupt worthiness of the communication request 602 (as represented by the aforementioned set of interrupt worthiness parameters 608) and the interruptability of the intended recipient and possibly other potential recipients (as represented by the aforementioned set of interruptability parameters 614) are provided to the decision making engine 312. The decision making engine 312 is configured to execute a decision making process that determines a selected set of delivery features 622 that are to be used by the data flow adaptation module 322 in formulating the modified communication request 604.

A first example of a delivery feature includes at least one final recipient for the modified communication request 604. The at least one final recipient for the modified communication request 604 may be the intended recipient, an alternate recipient, several recipients, depending on the outcome of the decision making process executed by the decision making engine 312. Thus, for example, the at least one final recipient may be an individual person or machine (e.g., Dr Jones), a class or group of people/machines sharing a common situational classification (e.g., "all cardiologists", "any cardiologist" or "the three most available cardiologists").

For instance, if the interruptability profile of the intended recipient (i.e., one of the interruptability parameters 614) is such that the intended recipient is highly interruptible and has only one (1) free minute of talk time, and if the interruptability profile of an alternate recipient is such that the alternate recipient is moderately interruptible but has twenty (20) free minutes of talk time, then depending on what needs to be conveyed, the decision making engine 312 might consider bypassing the intended recipient and attempting to reach the alternate recipient. On the other hand, if the specificity of the communication request (i.e., one of the interrupt worthiness parameters 608) is such that it requires the intended recipient—and only the intended recipient—to answer the communication request, then the decision making engine 312 might have no choice but to try and reach the intended recipient, but may want to send both an email message and make a call attempt, just in case the intended recipient does not consider that the one (1) available minute is enough to justify answering the phone.

A second example of a delivery feature includes a selected format for the modified communication request 604, such as email message, text message, page attempt, call attempt, voice mail message, multimedia session or message, etc. The selected format for the modified communication request 604 may be the format in which the communication request 602 was received by the communication request receiving entity 208R, or it may differ as a result of the decision making process executed by the decision making engine 312. Furthermore, the choice of format may be calculated so as to minimize the impact of the interruption. Thus, for instance, the decision making engine 312 may decide that it is preferable to have the recipient respond verbally to a short voice message without taking his or her eyes off of the task at hand (e.g., surgery) rather than to stop the task to read an e-mail and type a reply. In another example, the message may be abbreviated. To take a specific example, an urgent and important communication request destined for a doctor who is in surgery can be automatically reformatted to a short audio or text message for delivery to the doctor over a headset, speaker, or heads-up display.

A third example of a delivery feature includes a selected timing for the modified communication request 604, such as instantaneous or delayed. When the selected timing for the modified communication request 604 is "delayed", then an indication of the amount of delay may be provided in terms of a number of seconds or minutes, for example.

Generally speaking, execution of the decision making process can be viewed as the quest for a set of delivery features that satisfy the interrupt worthiness of the communication request 602, while respecting the interruptability of the final recipient. If exactly one candidate set of delivery features is found, then it becomes the selected set of delivery features 622 that is used by the data flow adaptation module 322 in formulating the modified communication request 604. If more than one candidate set of delivery features is found, then a selection process can be applied in order to select the "best" (according to certain selection criteria which may be set in conjunction with the policies of the healthcare facility) set of delivery features; the selected set of delivery features 622 is then used by the data flow adaptation module 322 in formulating the modified communication request 604.

The selection criteria used to identify the "best" set of delivery features from among various candidate sets of delivery features, and the relative significance of those selection criteria, can be referred to as "interrupt policies and procedures" 624. The decision making engine 312 can receive or access the interrupt policies and procedures 624 from an interrupt policies and procedures database 626, which may be implemented as part of the institutional context processing engine 310, or as a stand-alone entity.

As mentioned above, the selected set of delivery features 622 is provided to the data flow adaptation module 322, which is responsible for modifying the communication request 602 in accordance with the delivery features in the selected set of delivery features 622. Specifically, this amounts to causing delivery of the modified communication request 604 to the final recipient, in the selected format and with the selected timing, via the communication request delivering entity 208D.

EXAMPLES

Using the above examples of interrupt worthiness parameters 608 and interruptability parameters 614, various scenarios can be explored to illustrate non-limiting examples of operation of the decision making engine 312 when executing the communication request management service. In each case, a sender wishes to reach an intended recipient.

Scenario I:

Consider that Dr. Barbara is working within a workflow that involves a consultation with a patient for the first time. At present, Dr. Barbara is learning about the patient's symptoms. Dr. Walters wishes to send an email Dr. Barbara to tell her that he has found the answer to a question that Dr. Barbara had asked him yesterday, but requesting that she call back Dr. Walters for confirmation that she has understood the answer.

Example interrupt worthiness parameters 608 derived by the interrupt worthiness evaluator 606 and that may characterize this communication request may be as follows:

importance of communication request: Medium (Dr. Barbara expressed some interest when asking the question yesterday);

urgency of communication request: Low (the answer offered by Dr. Walters is informational and does not require a reply by Dr. Barbera);

specificity of communication request: High (only Dr. Barbera will benefit from the answer offered by Dr. Walters).

Example interruptability parameters 614 derived by the interruptability evaluator 612 and that may characterize Dr. Barbara (the intended recipient) may be as follows:

criticality level of current and next/future task(s): Medium (the current task in the workflow is important, but not mission-critical);

interruptability profile: moderately busy now, will be available in 5 minutes (average amount of time spent learning symptoms in this type of workflow; next task is transition to following patient, therefore an interruption is tolerated);

list of preferred interrupters: List does not include Dr. Walters.

Based on the above interrupt worthiness parameters 608 and interruptability parameters 614, the decision making engine 312 may produce the following candidate sets of delivery features (which include format, delay and final recipient):

Candidate set #1:
format: email
delay: none
final recipient: Dr. Barbara
Candidate set #2:
format: page
delay: 5 minutes
final recipient: Dr. Barbara Because there are plural candidate sets of delivery features, the decision making engine turns to the interrupt policies and procedures. Assume that for the purposes of the present example, due to the fact that Dr. Walters has requested that Dr. Barbara call him back, the interrupt policies and procedures state will choose a paging format over the email format. This results in candidate set #2 becoming the selected set of delivery features, which are provided to the data flow adaptation module 322.

Scenario II:

Consider now that Dr. Casey, who is a cardiologist, is in workflow that involves surgery on a patient. At present, Dr. Casey is in the operating room at a critical point in the surgery. Dr. Pearlman, who takes care of his patient Mrs. Dobson, realizes that she is having a failure and requires urgent assistance from a cardiologist. Since he knows that Dr. Casey is on duty, Dr. Pearlman places an urgent call for assistance to Dr. Casey. Assume that there is also another cardiologist on duty, Dr. Fernandez, who is currently on lunch break.

Example interrupt worthiness parameters 608 derived by the interrupt worthiness evaluator 606 and that may characterize this communication request may be as follows:

importance of communication request: High (any potential heart condition is considered a serious matter);

urgency of communication request: High (without a cardiologist's quick attention, Mrs. Dobson may become sick or die);

specificity of communication request: Low (any cardiologist will do).

It is noted that some of the interrupt worthiness parameters 608 may be derived based on factors such as patient vital signs, proximity of the patient (Mrs. Dobson) to the clinician who made the communication request (Dr. Pearlman), and so on.

Example interruptability parameters 614 derived by the interruptability evaluator 612 and that may characterize Dr. Casey (the intended recipient) may be as follows:

criticality level of current and next/future task(s): High (the current task in the workflow is mission-critical);

interruptability profile: Very busy now, available in 2 hours (average amount of time remaining before completion of the surgery)

list of preferred interrupters: Dr. Pearlman has a higher Preference Level than most other clinicians.

Example interruptability parameters 614 derived by the interruptability evaluator 612 and that may characterize Dr. Fernandez (the cardiologist on lunch break) may be as follows:

criticality level of current and next/future task(s): Low interruptability profile: Not busy now and not scheduled to be busy for the next hour list of preferred interrupters: Dr. Pearlman does not have any particular Preference Level from the point of view of Dr. Fernandez.

Based on the above interrupt worthiness parameters 608 and interruptability parameters 614, the decision making engine 312 may produce the following set of delivery features (which include format, delay and final recipient):

Candidate set #1:
format: page
delay: none
final recipient: Dr. Fernandez

In the above example, only one candidate set of delivery features was generated by the decision making engine 312. This results in candidate set #1 becoming the selected set of delivery features, which are provided to the data flow adaptation module 322. It is noted that the final recipient of the modified communication request is Dr. Fernandez, who is a cardiologist and will is expected to be available to quickly respond to Dr. Pearlman's call for assistance, thus leading to a positive care outcome for Mrs. Dobson.

Therefore, it will be appreciated that embodiments of the present invention provide a method and system for managing communication requests in an institutional setting such as a healthcare facility, where the communication requests can come in a wide variety of formats and with varying degrees of criticality.

Figure 6A:
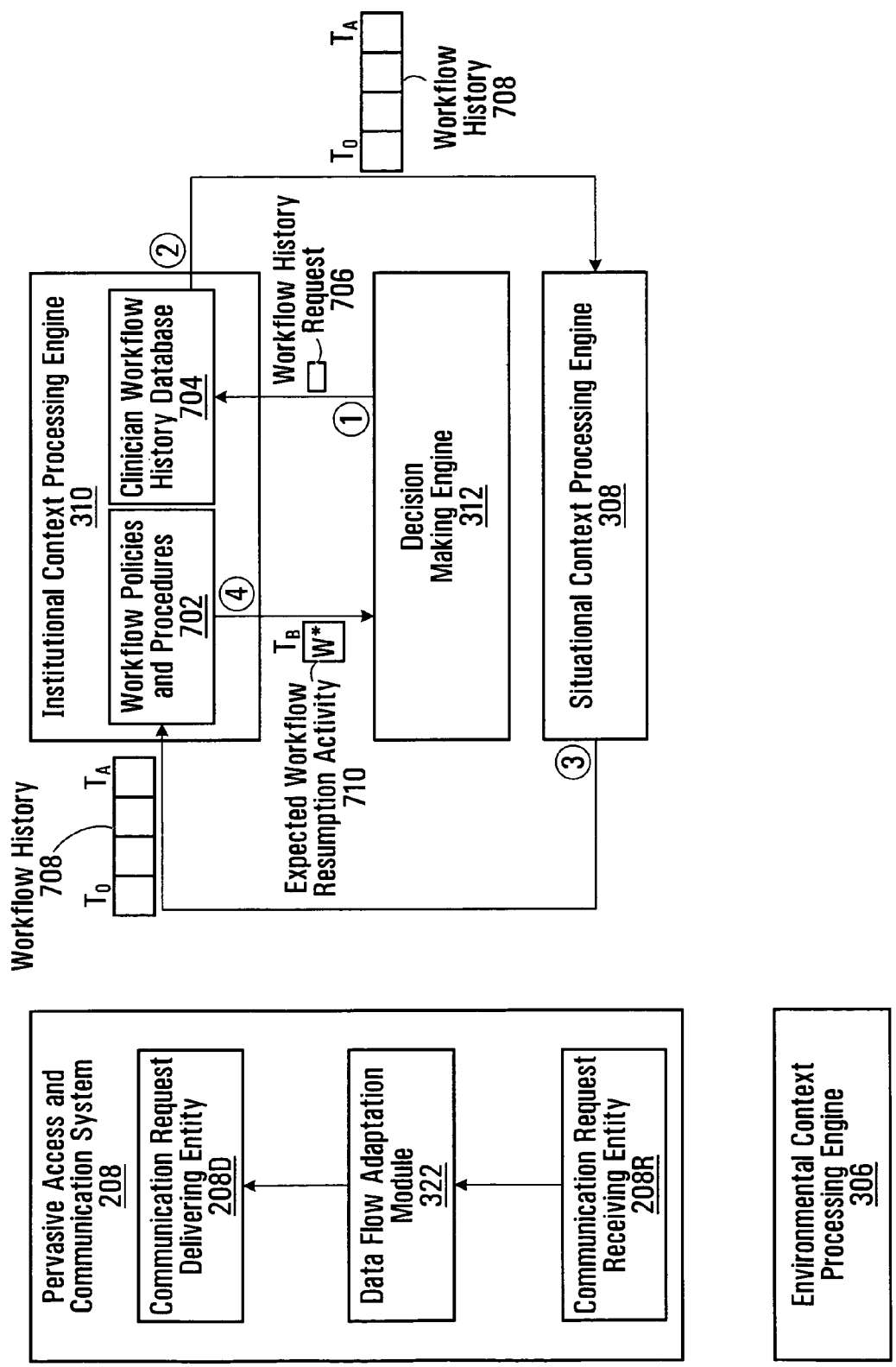
FIG. 6A is a block diagram depicting entities of the environment- and context-aware system that participate in determining expected future steps in the resumption of a workflow interrupted by a communication request.
Figure 6B:
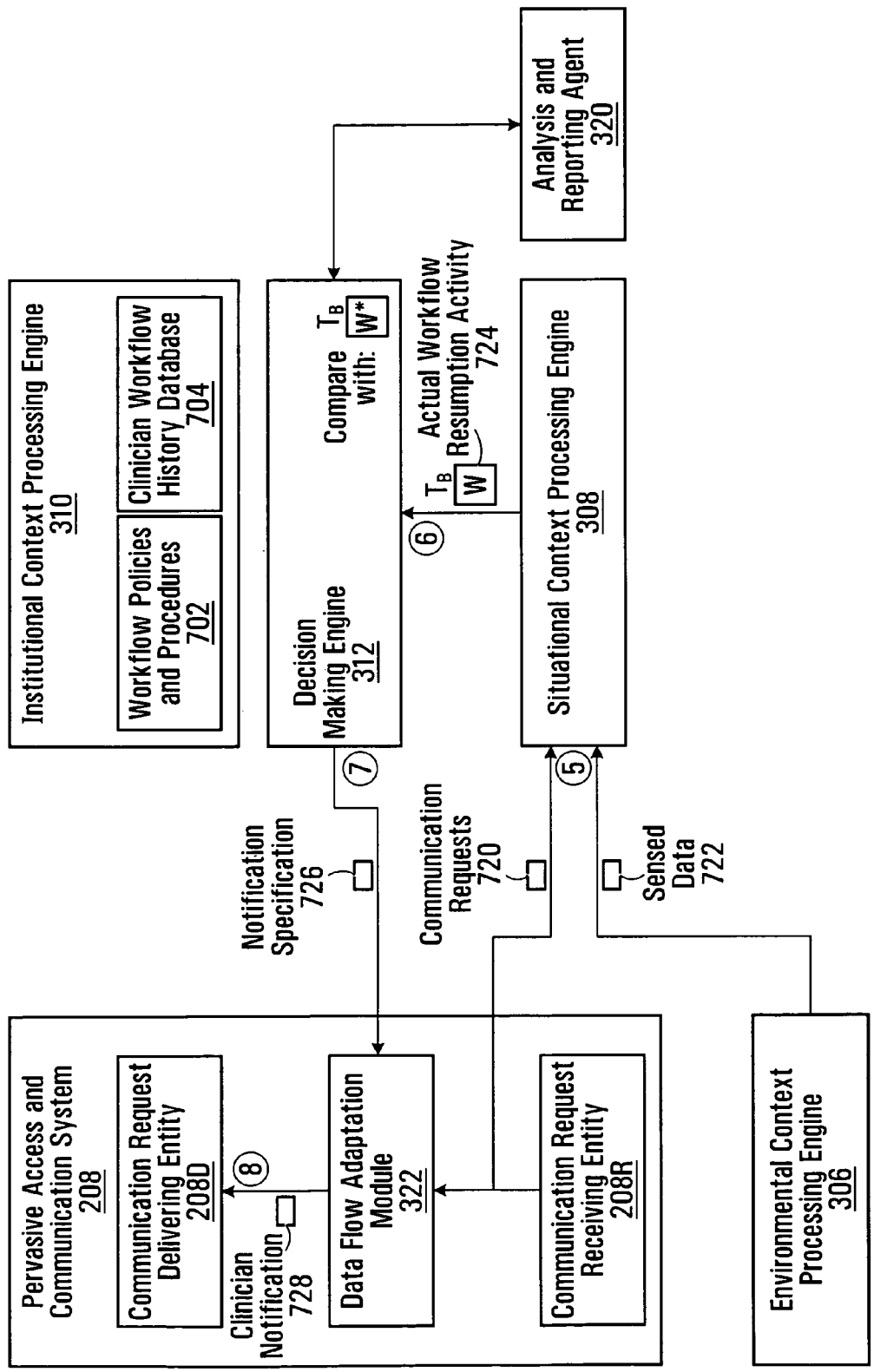
FIG. 6B is a block diagram depicting entities of the environment- and context-aware system that participate in notifying a user and/or an analysis and reporting agent when the actual steps being performed by the user are inconsistent with the future steps determined as in FIG. 6A.

A further refinement to the communication request management service is now described with reference to FIG. 6A and FIG. 6B. Specifically, the ECAS 12 can provide a process continuity support tool in order to enhance process continuity and identify missing or duplicated steps sufficiently early in order to prevent problems from escalating. Specifically, it is recognized that resuming a workflow exactly from a past state while circumstances that surround the interrupted workflow may have changed (e.g., handing off to a substitute clinician) could lead to errors and inefficiency. By using contextual information and saving the current workflow state, use of the ECAS 12 helps to prevent workflow errors. For example, the ECAS 12 could trigger a rapid review of the workflow up to the point of the interruption so that the substitute clinician can have a better grasp of what tasks the departing clinician did, and did not, complete.

Accordingly, it is first recalled that as described above with reference to FIG. 5, the modified communication request 604 is delivered to the final recipient, in accordance with delivery features that are determined by the decision making engine 312. Following this, various entities of the ECAS 12 participate in determining expected future steps in the resumption of a workflow interrupted by the modified communication request 604. In particular, at step 1, having obtained an indication that the workflow has been interrupted at time $T_4$, the decision making engine 312 requests the workflow history from the institutional context processing engine 310. This can be achieved by sending a message 706 to a clinician workflow history database 704. The message 706, which includes a workflow history request, may also include an identity of the final recipient of the modified communication request 604, say, Dr. Burns.

In response, at step 2, the clinician workflow history database 704 issues a workflow history 708 to the situational context processing engine 308. The workflow history 708 includes a series of steps that were recently performed (until time $T_A$) by Dr. Burns in the context of a specific workflow. For example the specific workflow could be open-heart surgery consisting of twelve (12) basic steps, and Dr. Burns may have performed steps 1 through 4. Thus the workflow history 708 could be the details of the first four steps of the workflow, including details of where and when Dr. Burns scrubbed in, what patient he is scheduled to operate on, etc.

At step 3, the situational context processing engine 308 sends the workflow history 708 to the institutional context processing engine 310, more specifically, to a workflow policies and procedures database 702 in the institutional context processing engine 310. The workflow policies and procedures database 702 stores information regarding future steps that should be performed by someone (although not necessarily Dr. Burns) having performed steps 1 through 4 of the workflow in the manner that they were performed by Dr. Burns. In a specific non-limiting example, the workflow policies and procedures database 702 returns expected workflow resumption activity 710 that represents one or more tasks W* to be performed starting at time $T_B$. At step 4, the expected workflow resumption activity 710 is provided to the decision making engine 312 for further processing, as now described with additional reference to FIG. 6B.

Specifically, at step 5, the situational context processing engine 308 receives information regarding actual workflow resumption activity, which can be executed by Dr. Burns or another clinician who took over from Dr. Burns after the interruption (hereinafter the "resuming clinician"). This information can be accumulated, collated, synthesized and fused on the basis of communication requests 720 obtained from the pervasive access and communication system 208 and also on the basis of sensed data 722 obtained from the environmental context processing engine 306. The situational context processing engine 308 assesses the situational context of the resuming clinician, determines the actual workflow resumption activity 724 and provides it to the decision making engine 312 at step 6.

The decision making engine 312 carries out a comparison between the expected workflow resumption activity 710 and the actual workflow resumption activity 724 following the interruption. On a basis of this comparison, the decision making engine 312 may determine that the resuming clinician needs to be notified. More specifically, the comparison may involve determining a degree of consistency between the actual workflow resumption activity and the expected workflow resumption activity.

If the degree of consistency is below a certain threshold, this may be indicative that the resuming clinician is off track as regards this particular workflow. This could be particularly evident when the resuming clinician has omitted or duplicated a step. In this case, the decision making engine 312 may cause issuance of a notification 728 at step 8. This can be achieved by providing a set of delivery features 726 to the previously described data flow adaptation module 322 at step 7. The set of delivery features 726 may include a final recipient for the notification 728, a selected format for the notification 728 and a selected timing for the notification 728. In some non-limiting examples, the contents of the notification 728 may indicate "Please confirm that you wish to duplicate the step of _____" or "Please confirm that you wish to bypass the step of _____", which can serve the function of decision support, rather than decision criticism.

On the other hand, if the degree of consistency is above a certain threshold, this may be indicative that the resuming clinician is on track as regards this particular workflow, and the decision making engine 312 may prepare for subsequent steps in the actual workflow resumption activity by re-executing step 3 and those subsequent thereto (see FIG. 6A), this time with a workflow that includes the most recent actual workflow resumption activity 724 (i.e., up until time $T_B$).

Alternatively, if the degree of consistency is above a certain threshold, or is above the certain threshold for a prolonged period of time, this may be indicative that the resuming clinician is unlikely to commit an error as regards this particular workflow. In such a case, the decision making engine 312 may cease to provide process continuity support by ceasing to monitor the communication requests 720 and the sensed data 722.

It is also within the scope of the present invention for the situational context processing engine 312 to continually assess the situational context in which the interruption has been resumed based on the situational context communication requests 720 and the sensed data 722. The decision making engine 312 may continually carry out comparisons between the expected workflow resumption activity 710 and the actual workflow resumption activity 724 on an ongoing basis and provide the results to the analysis and reporting agent 320 in the form of messages, for example.

While specific embodiments of the present invention have been described and illustrated, it will be apparent to those skilled in the art that numerous modifications and variations can be made without departing from the scope of the invention as defined in the appended claims.

The invention claimed is:

1. A machine-implemented method, comprising:
   receiving, at a communication request receiving entity, a communication request destined for an intended recipient;
   accessing at least one information system to determine, at an interrupt worthiness evaluator, an interrupt worthiness of the communication request and to determine, at an interruptability evaluator, at least one interruptability parameter indicative of an interruptability of the intended recipient;
   determining, at a decision making engine, at least one delivery feature based on the interrupt worthiness of the communication request and the interruptability of the intended recipient; and
   causing, at a communication request delivering entity, delivery of the communication request over a communication system in accordance with the at least one delivery feature.

2. The method defined in claim 1, wherein determining the interrupt worthiness of the communication request comprises determining at least one interrupt worthiness parameter.

3. The method defined in claim 2, wherein the at least one interrupt worthiness parameter is determined based on information intrinsic to the communication request.

4. The method defined in claim 3, wherein the information intrinsic to the communication request comprises an identity of the intended recipient.

5. The method defined in claim 3, wherein the communication request originates from and specifies a sender, wherein the information intrinsic to the communication request comprises an identity of the sender.

6. The method defined in claim 3, wherein the communication request originates from a sender and includes ancillary information provided by the sender, wherein the information intrinsic to the communication request comprises the subjective information provided by the sender.

7. The method defined in claim 6, wherein the ancillary information provided by the sender comprises at least one of a sender-specified importance of the communication request, a sender-specified urgency of the communication request, a sender-specified specificity of the communication request and a sender-specified confidentiality of the communication request.

8. The method defined in claim 3, wherein the communication request encodes a message, wherein the information intrinsic to the communication request comprises the message.

9. The method defined in claim 8, the method further comprising applying a message processing function to decode the message in the communication request.

10. The method defined in claim 3, wherein the at least one interrupt worthiness parameter is further determined based on information extrinsic to the communication request.

11. The method defined in claim 10, wherein the information extrinsic to the communication request comprises information held in at least one of a hospital information system and a hospital clinical information system.

12. The method defined in claim 11, wherein the information extrinsic to the communication request is determined by a situational context processing engine based on access to the hospital information system and the hospital clinical information system via an institutional context processing engine.

13. The method defined in claim 10, wherein the information extrinsic to the communication request comprises situational information regarding the intended recipient.

14. The method defined in claim 13, wherein the situational information regarding the intended recipient includes at least one of a location of the intended recipient, a location of patients associated with the intended recipient, a skill set of the intended recipient, a schedule of the intended recipient and an actual workflow situation of the intended recipient.

15. The method defined in claim 10, wherein the communication request originates from a sender, wherein the information extrinsic to the communication request comprises situational information regarding the sender.

16. The method defined in claim 15, wherein the situational information regarding the sender includes at least one of a location of the sender, a location of patients associated with the sender, a skill set of the sender, a schedule of the sender, an actual workflow situation of the sender, an emotional or physical state of the intended recipient and a relationship between the sender and the intended recipient.

17. The method defined in claim 10, wherein the information extrinsic to the communication request comprises environmental information.

18. The method defined in claim 10, wherein the information extrinsic to the communication request comprises historical information.

19. The method defined in claim 10, wherein the at least one interrupt worthiness parameter includes an importance of the communication request.

20. The method defined in claim 10, wherein the at least one interrupt worthiness parameter includes an urgency of the communication request.

21. The method defined in claim 10, wherein the at least one interrupt worthiness parameter includes a specificity of the communication request.

22. The method defined in claim 10, wherein the at least one interrupt worthiness parameter includes degree of life impact or workflow criticality of the communication request.

23. The method defined in claim 1, wherein the at least one interruptability parameter is determined based on information extrinsic to the communication request.

24. The method defined in claim 23, wherein the information extrinsic to the communication request comprises information held in at least one of a hospital information system and a hospital clinical information system.

25. The method defined in claim 24, wherein the information extrinsic to the communication request is determined by a situational context processing engine based on access to the hospital information system and the hospital clinical information system via an institutional context processing engine.

26. The method defined in claim 23, wherein the information extrinsic to the communication request comprises situational information regarding the intended recipient.

27. The method defined in claim 26, wherein the situational information regarding the intended recipient includes at least one of a location of the intended recipient, the intended recipient's duration on shift, a location of patients associated with the intended recipient, a skill set of the intended recipient, a schedule of the intended recipient, an actual workflow situation of the intended recipient and an emotional or physical state of the intended recipient.

28. The method defined in claim 23, wherein the information extrinsic to the communication request comprises information held in at least one of a hospital information system and a hospital clinical information system.

29. The method defined in claim 1, further comprising identifying a task being performed or to be performed by the intended recipient and determining a criticality level of said task, wherein the at least one interruptability parameter includes said criticality level.

30. The method defined in claim 1, wherein the at least one interruptability parameter includes a profile descriptive of an interruptability tolerance over future time.

31. The method defined in claim 1, further comprising (i) identifying a workflow for the intended recipient, the workflow including a sequence of tasks; (ii) identifying which of the tasks is currently being performed by the intended recipient; and (iii) determining an expected amount of time before an interruption is tolerated, wherein the at least one interruptability parameter includes said expected amount of time.

32. The method defined in claim 1, wherein the communication request originates from a sender, wherein the method further comprises consulting a database to determine data regarding a preference of the intended recipient to be interrupted by said sender, and wherein at least one said interruptability parameter is determined based at least in part on said preference.

33. The method defined in claim 1, wherein the at least one delivery feature includes a format for delivery of the communication request.

34. The method defined in claim 33, wherein said format is one of: an email message, a call attempt, a text message, a video message, a multimedia message, a voice mail message, a page attempt and combinations thereof.

35. The method defined in claim 1, wherein the communication request is received from a sender in a first format, wherein the format for delivery of the communication request is different from the first format.

36. The method defined in claim 1, wherein the at least one delivery feature includes a delay before delivery of the communication request.

37. The method defined in claim 1, wherein the at least one delivery feature includes identification of a final recipient to which the communication request is delivered.

38. The method defined in claim 37, wherein the final recipient is the intended recipient.

39. The method defined in claim 37, wherein the final recipient is different from the intended recipient.

40. The method defined in claim 1, wherein the at least one delivery feature includes identification of a plurality of final recipients to which the communication request is delivered.

41. The method defined in claim 1, wherein the plurality of final recipients share a common situational classification.

42. The method defined in claim 1, wherein determining the at least one delivery feature comprises establishing at least one delivery feature set that satisfies the interrupt worthiness of the communication request, while respecting the interruptability of a set of at least one potential recipient that includes the intended recipient.

43. The method defined in claim 42, wherein when said at least one delivery feature set comprises a single delivery feature set, and wherein the method further comprises setting the at least one delivery feature in the single delivery feature set as the at least one delivery feature in accordance with which the communication request is to be delivered over the communication system.

44. The method defined in claim 42, wherein when at least one delivery feature set comprises multiple delivery feature sets, and wherein the method further comprises (i) selecting one of the multiple delivery feature sets in accordance with a set of interrupt policies and procedures; and (ii) setting the at least one delivery feature in the selected delivery feature set as the at least one delivery feature in accordance with which the communication request is to be delivered over the communication system.

45. The method defined in claim 44, further comprising obtaining the set of interrupt policies and procedures from an institutional context processing engine.

46. The method defined in claim 1, wherein the intended recipient is a human.

47. A computer-readable storage medium comprising computer-readable instructions for instructing a computing device to:

determine an interrupt worthiness of a communication request destined for an intended recipient;

determine at least one interruptability parameter indicative of an interruptability of the intended recipient;

determine at least one delivery feature based on the interrupt worthiness of the communication request and the interruptability of the intended recipient; and cause delivery of the communication request over a communication system in accordance with the at least one delivery feature.

48. A system, comprising:

a communication request receiving entity configured to receive a communication request destined for an intended recipient;

an interrupt worthiness evaluator configured to determine an interrupt worthiness of the communication request;

an interruptability evaluator configured to determine at least one interruptability parameter indicative of an interruptability of the intended recipient;

a decision making engine configured to determine at least one delivery feature based on the interrupt worthiness of the communication request and the interruptability of the intended recipient; and a communication request delivering entity configured to deliver the communication request in accordance with the at least one delivery feature.

49. A system, comprising:

means for determining an interrupt worthiness of the communication request;

means for determining at least one interruptability parameter indicative of an interruptability of the intended recipient;

means for determining at least one delivery feature based on the interrupt worthiness of the communication request and the interruptability of the intended recipient; and means for causing delivery of the communication request over a communication system in accordance with the at least one delivery feature.

\* \* \* \* \*